(12) United States Patent
Ji et al.

(10) Patent No.: US 9,687,501 B2
(45) Date of Patent: **\*Jun. 27, 2017**

(54) MODIFIED STARCH MATERIAL OF BIOCOMPATIBLE HEMOSTASIS

(71) Applicants: Xin Ji, Shanghai (CN); Cheng Xing, Shanghai (CN); Xueshen Shi, Shanghai (CN); Jianping Chen, Shanghai (CN)

(72) Inventors: Xin Ji, Shanghai (CN); Cheng Xing, Shanghai (CN); Xueshen Shi, Shanghai (CN); Jianping Chen, Shanghai (CN)

(73) Assignee: Xin Ji, Shanghai (CN)

( \* ) Notice: Subject to any disclaimer, the term of this patent is extended or adjusted under 35 U.S.C. 154(b) by 0 days.

This patent is subject to a terminal disclaimer.

(21) Appl. No.: 13/894,396

(22) Filed: May 14, 2013

(65) Prior Publication Data

US 2013/0251996 A1    Sep. 26, 2013

Related U.S. Application Data

(62) Division of application No. 12/228,029, filed on Aug. 8, 2008.

(51) Int. Cl.
| | | |
|---|---|---|
| A61K 31/718 | (2006.01) | |
| A61L 24/00 | (2006.01) | |
| A61L 26/00 | (2006.01) | |
| A61K 9/14 | (2006.01) | |
| C08L 3/18 | (2006.01) | |
| C08L 3/04 | (2006.01) | |
| C08L 89/06 | (2006.01) | |
| C08B 31/12 | (2006.01) | |
| C08B 31/08 | (2006.01) | |
| C08B 31/02 | (2006.01) | |
| C08B 33/04 | (2006.01) | |
| C08B 31/10 | (2006.01) | |
| C08B 31/16 | (2006.01) | |
| C08B 35/02 | (2006.01) | |
| C08B 33/06 | (2006.01) | |
| C08B 35/06 | (2006.01) | |
| C08B 35/04 | (2006.01) | |
| C08B 33/02 | (2006.01) | |
| C08B 31/04 | (2006.01) | |
| C08B 30/20 | (2006.01) | |
| C08B 31/00 | (2006.01) | |
| C08B 30/00 | (2006.01) | |
| A61K 31/738 | (2006.01) | |
| A61L 24/08 | (2006.01) | |
| A61K 45/06 | (2006.01) | |
| A61K 9/19 | (2006.01) | |
| C08B 31/06 | (2006.01) | |
| A61K 9/00 | (2006.01) | |

(52) U.S. Cl.
CPC ............. *A61K 31/718* (2013.01); *A61K 9/14* (2013.01); *A61K 9/19* (2013.01); *A61K 31/738* (2013.01); *A61K 45/06* (2013.01); *A61L 24/0036* (2013.01); *A61L 24/08* (2013.01); *A61L 26/0023* (2013.01); *A61L 26/0085* (2013.01); *C08B 30/00* (2013.01); *C08B 30/20* (2013.01); *C08B 31/00* (2013.01); *C08B 31/003* (2013.01); *C08B 31/02* (2013.01); *C08B 31/04* (2013.01); *C08B 31/08* (2013.01); *C08B 31/10* (2013.01); *C08B 31/12* (2013.01); *C08B 31/16* (2013.01); *C08B 33/02* (2013.01); *C08B 33/04* (2013.01); *C08B 33/06* (2013.01); *C08B 35/02* (2013.01); *C08B 35/04* (2013.01); *C08B 35/06* (2013.01); *C08L 3/04* (2013.01); *C08L 3/18* (2013.01); *C08L 89/06* (2013.01); *A61K 9/0014* (2013.01); *A61L 2400/04* (2013.01); *A61L 2430/34* (2013.01); *Y10T 428/2982* (2015.01)

(58) Field of Classification Search
CPC ......... A61K 31/718; A61K 9/14; A61L 24/08; A61L 26/0023
See application file for complete search history.

(56) References Cited

U.S. PATENT DOCUMENTS

| | | | | |
|---|---|---|---|---|
| 5,079,354 | A * | 1/1992 | Gross et al. | 536/111 |
| 6,060,461 | A * | 5/2000 | Drake | A61K 31/721 |
| | | | | 514/54 |
| 2005/0256306 | A1* | 11/2005 | Woo et al. | 536/105 |
| 2007/0248653 | A1* | 10/2007 | Cochrum et al. | 424/445 |

OTHER PUBLICATIONS

Swinkels, J.J.M., Starch/Starke, 1985, 37, p. 1-5.*

\* cited by examiner

*Primary Examiner* — Jonathan S Lau
(74) *Attorney, Agent, or Firm* — Raymond Y. Chan; David and Raymond Patent Firm

(57) ABSTRACT

A modified starch material is arranged for biocompatible hemostasis, biocompatible adhesion prevention, tissue healing promotion, absorbable surgical wound sealing and tissue bonding, when applied as a biocompatible modified starch to the tissue of animals. The modified starch material produces hemostasis, reduces bleeding of the wound, extravasation of blood and tissue exudation, preserves the wound surface or the wound in relative wetness or dryness, inhibits the growth of bacteria and inflammatory response, minimizes tissue inflammation, and relieves patient pain. Any excess modified starch not involved in hemostatic activity is readily dissolved and rinsed away through saline irrigation during operation. After treatment of surgical wounds, combat wounds, trauma and emergency wounds, the modified starch hemostatic material is rapidly absorbed by the body without the complications associated with gauze and bandage removal.

4 Claims, 10 Drawing Sheets

Fig. 12

|  | Arista™ | 66# |
|---|---|---|
| water absorption ability (ml/s) (first 20s) | 0.011 | 0.056 |
| water absorption ability (ml/s) (second 20s) | 0.008 | 0.04 |
| water absorption ability (ml/s) (third 20s) | 0.007 | 0.03 |
| saturation rate of water absorption (%) (20s) | 28.21 | 58.42 |
| saturation rate of water absorption (%) (40s) | 41.03 | 84.74 |
| saturation rate of water absorption (%) (60s) | 50 | 94.74 |

Fig. 13

|  | 88# | 66# | Arista™ |
|---|---|---|---|
| adhesion work index g·sec (25% saturation rate) | 420.9 | 15 | 0.7 |
| adhesion work index g·sec (50% saturation rate) | 307.4 | 78.9 | 4 |
| adhesion work index g·sec (100% saturation rate) | 75.2 | 68.1 | 17 |

Fig. 14

|  | Arista™ | 66# |
|---|---|---|
| Viscosity(mPa·s) | 2 | 557.9 |

Fig. 15

| sample | water absorbency |
|---|---|
| 51# | 17.5 |
| 66# | 23 |
| 66#+ | 23.5 |
| 88# | 4.4 |
| Arista™ | 12.8 |

Fig. 16

|  | Pressing with gauze | Arista™ | 66# | 88# |
|---|---|---|---|---|
| Samples of successful hemostasis after pressing 60s | 0/10 | 0/10 | 1/10 | 4/10 |
| Samples of successful hemostasis after pressing 90s | 0/10 | 2/10 | 5/10 | 8/10 |
| Samples of successful hemostasis after pressing 120s | 0/10 | 3/10 | 9/10 | 10/10 |
| Samples of successful hemostasis after pressing 180s | 2/10 | 9/10 | 10/10 | 10/10 |

Fig. 17

|  | Blank control group | 66# group | Medical sodium hyaluronate SH group |
|---|---|---|---|
| Grade 0 | 0 | 2 | 4 |
| Grade 1 | 0 | 7 | 3 |
| Grade 2 | 0 | 1 | 3 |
| Grade 3 | 3 | 0 | 0 |
| Grade 4 | 8 | 2 | 1 |
| Average grade | 3.72 | 1.42* | 1.18* |

\* $P<0.05$ vs control group

Fig. 18

| group | healing score | mineral apposition rate(μm/d) | osteoid area(%) | mineralization bone area(%) | congenital absence area(%) |
|---|---|---|---|---|---|
| control group | 2.14±0.84 | 2.02±0.34 | 12.02±4.32 | 6.23±2.34 | 76.21±19.35 |
| 66# | 1.23±0.45* | 3.86±1.19* | 35.02±9.85* | 28.25±9.35* | 43.12±11.87* |
| 51# | 1.14±0.43* | 4.04±1.04* | 34.02±9.22* | 31.23±8.45* | 40.34±12.60* |
| bonewax | 1.86±0.65 | 2.87±0.84* | 22.02±6.32 | 16.23±6.86* | 58.34±17.64 |

\* *$P<0.05$ vs blank control group*

Fig. 20

|  | Sample (g) | Water absorbed (ml) | Water absorbency |
|---|---|---|---|
| composite hemostatic sponge F | 0.1 | 1.73 | 17.3 |
| composite hemostatic sponge G | 0.1 | 1.95 | 19.5 |
| composite hemostatic sponge H | 0.1 | 0.82 | 8.2 |
| composite hemostatic sponge I | 0.1 | 1.1 | 11.0 |

Fig. 19

| Experimental sample | volume density (g/cm³) | Water absorbency (times) | hydrophilicity | water absorption ability |
|---|---|---|---|---|
| hemostatic sponge A | 0.0679 | 19.7 | Hydrophilic, no equilibrium contact angle | Absorbing instantly |
| hemostatic sponge B | 0.0563 | 21.4 | Hydrophilic, no equilibrium contact angle | Absorbing instantly |
| hemostatic sponge C | 0.0688 | 22.8 | Hydrophilic, no equilibrium contact angle | Absorbing instantly |
| hemostatic sponge D | 0.0983 | 24.9 | Hydrophilic, no equilibrium contact angle | Absorbing instantly |
| hemostatic sponge E | 0.11179 | 7.6 | Hydrophilic, no equilibrium contact angle | Absorbing instantly |
| Absorbable gelatin sponge | 0.0099 | 40.6 | Hydrophobic, contact angle is 106° | Extremely slow |
| collagen sponge of KROD, ltd, Beijing | 0.0235 | 33.2 | Hydrophilic, no equilibrium contact angle | slow |
| SURGICEL of Johnson & Johnson, ltd (oxidized cellulose hemostatic gauze) | 0.0288 | 16.4 | Hydrophilic, no equilibrium contact angle | Absorbing instantly |
| chitosan hemostatic sponge of HEMCON, ltd, US | 0.1071 | 35.3 | Hydrophilic, no equilibrium contact angle | slow |

Fig. 21

| water absorbency (ml/s) | First 20s | Second 20s | Third 20s | Fourth 20s | Fifth 20s | Sixth 20s |
|---|---|---|---|---|---|---|
| composite hemostatic sponge F | 0.004 | 0.0035 | 0.0025 | 0.0025 | 0.0025 | 0.0025 |
| composite hemostatic sponge G | 0.0035 | 0.0035 | 0.003 | 0.0025 | 0.0025 | 0.0025 |
| composite hemostatic sponge H | 0.003 | 0.002 | 0.0007 | 0.0003 | 0.0003 | 0.0003 |
| composite hemostatic sponge I | 0.0008 | 0.0008 | 0.0008 | 0.0005 | 0.0003 | 0.0003 |
| Nanjing absorbable gelatin sponge | 0.0008 | 0.0008 | 0.0005 | 0.0003 | 0.0003 | 0.0003 |
| collagen sponge of KROD ltd, Beijing | 0.0017 | 0.0008 | 0.0005 | 0.0003 | 0.0003 | 0.0003 |

MODIFIED STARCH MATERIAL OF BIOCOMPATIBLE HEMOSTASIS

CROSS REFERENCE OF RELATED APPLICATION

This is a Divisional application that claims the benefit of priority under 35 U.S.C. §119 to a non-provisional application, application Ser. No. 12/228,029, filed Aug. 8, 2008.

BACKGROUND OF THE INVENTION

Field of Invention

The present invention relates to a modified starch material of biocompatible hemostasis, biocompatible adhesion prevention, tissue healing promotion, absorbable surgical sealing and tissue bonding, and more particularly to a modified starch material, which is absorbable by human beings and animals, and applied directly to wound surface of humans and mammals, including wound surface with blood or extravasate, to stanch blood, prevent adhesion, promote tissue healing, seal section of wound tissue, prevent bleeding and exudation of tissue fluid, bond tissue and organ wounded by trauma or operation, help repairing tissue, and avoid or reduce surgical suture.

Description of Related Arts

Surgical operations and trauma may create bleeding wounds, which can produce a risk of excess blood loss. Therefore, hemostats to control bleeding should be applied in a timely manner. It is a common to apply biocompatible, absorbable hemostatic agents to bleeding wound sites to achieve hemostasis (cessation of bleeding) in surgical procedures, trauma treatment and home self rescue. There is clinical benefit to provide patients a hemostatic agent which is safe, efficacious, easy to use, and cost effective.

Prior absorbable hemostats consist of the following classes of materials:

Hemostatic sponge class: gelatin sponge, collagen sponge, chitosan sponge, carboxymethyl cellulose sponge, thrombin and fibrin sponges;

Hemostatic gauze/hemostatic film class: oxidized cellulose gauze, oxidized regenerated cellulose gauze, oxidized cellulose gauze with carboxymethyl cellulose;

Hemostatic glue class: fibrin glue, synthetic glue;

Polysaccharide hemostatic powder class: microporous polysaccharide powder, chitosan powder, algae powder.

A detailed analysis of absorbable hemostats in common use is stated below:

1. Absorbable Gelatin Sponges and Collagen Sponges:

The gelatin sponge is extracted from animal tissue, and the main component of the gelatin sponge is animal collagen. The gelatin sponge has a hydrophilic and multi-porous structure to concentrate blood components by absorbing water in the blood to arrest bleeding. However, gelatin is a collagen-based material from animal extract and contains heterogenetic protein which may cause anaphylaxis, resulting in feverish symptoms in patients. Further, the human body absorbs the gelatin material very slowly, and on average requires more than four weeks to fully dissolve. Foreign agents with slow absorption times can be sites for infection, tissue inflammation, and wound healing retardation.

Collagen sponges, which are also extracted from animal tissue, promote blood coagulation by activating the endogenous coagulation cascade while also concentrating blood components by absorbing water in the blood.

Like the gelatin sponges, collagen sponges are also sourced from animal collagen and contain heterogenetic protein, which is slow to absorb in the human body. The collagen sponge may produce complications of anaphylaxis, slow healing and infections. Due to these clinical risks, applications of collagen sponges may be limited in the future.

2. Oxidized Cellulose Hemostatic Gauze and Oxidized Regenerated Cellulose Hemostatic Gauze:

Oxidized cellulose is a cellulose derivative. The hemostatic mechanism of oxidized cellulose is the concentration of blood components through the hygroscopic activity of oxidized cellulose, which stimulates blood coagulation as the carboxyl material combines with haemoglobin Fe to produce acidic hematin in the blood. The resulting brown gel seals capillary vessels and promotes hemostasis. Oxidized regenerated cellulose has the same mode of action as oxidized cellulose.

Oxidized cellulose is synthetic. Normal human tissue degrades oxidized cellulose slowly by metabolizing enzymes. This process generally requires 3-6 weeks depending on the dosage and the tissue location in the body. Oxidized cellulose may cause local infection and adversely affect local tissue healing. Patent application, China publication number CN1533751A, discloses a hemostatic wound dressing with a trade name of SURGICEL. SURGICEL includes a cellulose fabric and a multi-porous polymer substrate on the fabric surface which contacts the wound. The substrate contains biocompatible, water-soluble polymers. The fabric fibers are oxidized regenerated cellulose and the biocompatible, water-soluble polymers are polysaccharides. This hemostatic wound dressing consists primarily of oxidized cellulose, a slowly absorbing material in the human body.

3. Fibrin Glues:

Fibrin glues consist of fibrinogen, thrombin, aprotinin and calcium chloride. The hemostatic action relies mainly on the activation of fibrinogen by the thrombin to promote coagulation cascade. Fibrin sealants are a mixture of fibrinogen and thrombin and have been widely used in recent years. The thrombin and fibrin in fibrin glues are sourced from either animal or human blood components and therefore create the risk of anaphylaxis and viral infections such as hepatitis, AIDS, and BSE. Fibrin glues demonstrate weak adhesion when applied to wet, bleeding tissue and may be ineffective in the presence of active bleeding. Further, fibrin glues require special mixing, timing and storage condition.

4. Natural Biological Polysaccharide Products:

In recent years, natural, biological polysaccharide-based products have focused much attention. The natural biological polysaccharide products are derived from plant material and chitosans and usually presented in powder form. These products have good biocompatibility, no toxicity, no tissue irritation, and no risk of anaphylaxis or viral infection from animal or human components contained in other hemostats.

Chitosan/Chitin Products:

Chitosan products are typically available in high swelling and non-absorbable sponges. Chitosan is made from the crushed shells of crustaceans. Chitosan has rapid hydrophilic capability and can activate the blood coagulation mechanism through its strong ionic charge. However, due to a lack of human enzymes to degrade chitosan, chitosan-derived products will be confined to topical applications. There is no evidence that chitosan products have been used in clinic as absorbable surgical hemostats.

Microporous Polysaccharide Hemospheres (MPH):

In 2002, MEDAFOR, INC. in the USA developed an absorbable hemostatic material called Arista™ (U.S. Pat. No. 6,060,461), which consists of microporous polysaccharid particles (MPH). The microporous polysaccharide particles are made through the reaction of purified starch and epichlorohydrin, wherein the epichlorohydrin reacts with starch molecules. This reaction results in the formation of ethyl propanetriol which creates a glucose molecule cross-link to the 3D network structure.

There are a few disadvantages of the MPH hemostatic powder. Firstly, the delivery of MPH mainly focuses on local, easy-to-access wound sites but presents some difficulties for effective applications for deep, tortuous wounds, in particular the endoscopic procedures (such as minimally invasive surgery via endoscope and laparoscope). Secondly, during the production process, epichlorohydrin, a colorless, oily and toxic chemical, is employed to produce a required reaction. This production process is not environment friendly. The cost of production is relatively expensive. Thirdly, the hemostatic efficacy of MPH is not satisfactory in particular for profuse bleeding due to its low hydrophilic capacity and slow water absorption characteristic. Fourthly, the adhesiveness of the MPH to tissue is low following contacting with blood. The low viscosity, low adhesiveness of MPH following water absorption may reduce the hemostatic efficacy of MPH due to its weak sealing capability to wounded tissues and broken vessels. Fifthly, in the presence of active bleeding, the MPH powder can be easily washed away by blood flow if not compressed with a gauze on the top of powder. This gauze compression requirement adds an additional step in the hemostatic powder application technique and may risk re-bleeding when the gauze is removed. Therefore, MPH may have an unsatisfactory hemostatic efficacy for active bleeding.

SUMMARY OF THE INVENTION

An object of the present invention is to provide a biocompatible, modified starch composition and new uses of the modified starch in humans and/or animals as a topical and surgical hemostat. Hemostasis occurs immediately and effectively when the said hemostat contacts blood on wound sites.

Another object of the present invention is to provide a modified starch composition as an agent for anti-adhesion therapy, for promoting tissue healing, for sealing wounds and bleeding vessels, for adhesive sealing and tissue bonding, and for promoting bacteriostatic and anti-inflammatory effects on bleeding wound sites. In addition to its hemostatic performance, the application of the invention will support anti-adhesions, tissue healing, surgical sealing and tissue bonding and reinforcement when the bleeding wound is on the skin surface or in the internal organs and whether the application is in an open surgical operation, trauma treatment, or delivered under laryngoscope, endoscope, and laparoscope.

Another object of the present invention is to provide methods of producing the modified starch hemostatic composition and the technological formula to manufacture the modified starch in the following formats: powder, sponge, foam, gel, film and others. These formats do fulfill dynamic surgical hemostatic requirements, and are easy to use.

Another object of the present invention is to provide the methods, process and techniques to modify the starch composition to satisfy important physical and chemical properties and characteristics, technical parameters and technical indices required for a hemostat, surgical sealant, an agent for anti-adhesion, tissue healing, tissue adhesive sealing and tissue bonding. The modified starch hemostatic composition is absorbed by humans and animals, is safe and effective, and can be degraded rapidly.

In addition, the modified starch in the present invention can be used as a biocompatible, an anti-adhesion material, a tissue healing agent, a surgical sealant, and a tissue bonding/reinforcement substance for tissue repair.

The technical formulas in the present invention fulfill the foregoing performance requirements with modified starch applications as a biocompatible hemostatic material with mechanisms that include dissolving or swelling in water and the subsequent formation of adhesive glue or adhesive gel.

The mechanism further includes a modified starch acquisition of hydrophilic groups in its molecular chains through the modification process.

When the hydrophilic and enhanced adhesive modified starch according to the present invention is applied to bleeding wound sites, it rapidly absorbs water in the blood and concentrates blood components. Meanwhile, this interaction creates an adhesive matrix formed with the blood and plasma which adheres to the bleeding wound, mechanically seals the broken blood vessels and stops bleeding.

The modified starch material according to the present invention includes starch modified physically, chemically, naturally, or enzymatically, and starch modified repeatedly with at least one of the above methods or a combination of two or more of the above methods.

The physical modifying process according to the present invention comprises irradiation, mechanical, and steam treatment.

Physically modified starch, for example, a pre-gelatinized starch treated solely with spray drying or irradiation process, is remarkably safe as a bio-absorbable, hemostatic material since it is not treated with any chemical agents.

The starch can be pre-gelatinized by the following physical modifying processes: a) dry-process, such as an extrusion process and a roller process; b) wet-process, such as a spray drying process.

Specifically, after heating the raw starch with a measured amount of water, starch granules swell to a pasty substance, regularly arranged micelle of starch are broken, crystallites disappear, and the resulting composition is easily degraded under the process of amylase. The pre-gelatinized starch is able to swell and/or dissolve in cold or room temperature water and form an adhesive paste whose retrogradation is lower than that of raw starch, affording easier handling during the production process.

Raw starch can be pre-gelatinized through solely a physical modification process without adding any chemical agents and becomes a hemostatic material with enhanced hydrophilic and adhesive properties.

The pre-gelatinized starch of the present invention is safe, non-toxic, and has no adverse side effects. The pre-gelatinized starch is readily degraded and metabolized by enzymes in the body. The pre-gelatinized material of the present invention is safe and biocompatible.

The chemical modifying according to the present invention includes acidolysis, oxidation, esterification, etherification, cross-linking, chemical agent grafting, or multiple modifying processes including at least two of the above processes, or one of the above modifying processes performed at least twice.

In the present invention, by adding the functional group on the raw starch glucose units with chemical agents, e.g. by carboxylation modification, or hydroxylation modification, the starch captures hydrophilic groups in its molecular structure and obtains hydrophilic properties. By using bifunctional or polyfunctional chemical agents to cross-link the raw starch macromolecules or grafting external macromolecurlar hydrophilic groups to the raw starch, the starch acquires enhanced hydrophilic properties and viscosity/adhesiveness in a water solution. The viscosity of modified starch relates to the raw starch origin and the degree of substitution of external and cross-linked or grafted functional groups, etc. . . . . . When contacting blood, the hydrophilic and adhesive properties of the modified starch of the present invention produce a "starch-blood coagulation matrix" with strong adhesive characteristics which can seal wounded tissue and stop bleeding. In addition, the interaction between the formed blood coagulation matrix and the functional groups of tissue proteins causes the "starch-blood coagulation matrix" to adhere to and seal the wounded tissue, resulting in hemostasis.

Specifically, the described modified starch contains one or more groups of pre-gelatinized starch, acid modified starch, dextrin, oxidized starch, esterified starch, etherified starch, and cross-linked starch.

The described hemostatic composition comprises two or more modified starches to satisfy the physical and chemical properties of a hemostatic agent, where the weight ratio of the two modified starch groups can be 99:1~1:99.

Specifically, the weight ratio of the two modified starch groups can be: 95:5, 90:10, 85:15, 80:20, 75:25, 70:30, 65:35, 60:40, 55:45, or 50:50.

The main physical parameters of the modified starch, according to the present invention, are provided below:

The modified starch of the present invention has a molecular weight over 15,000 Daltons (for instance, 15,000~2,000,000 Daltons).

The modified starch of the present invention has a water absorbency capacity not lower than one time its weight (i.e. 1 gram of described modified starch can absorb 1 gram or more of water); whereas it can be 1~500 times generally and 2~100 times preferably.

The modified starch composition of the present invention includes, but not limited to, at least one carboxymethyl starch, hydroxyethyl starch, and cationic starch.

For example, the carboxymethyl starch is a polymer of linear structure as expressed in the following formula:

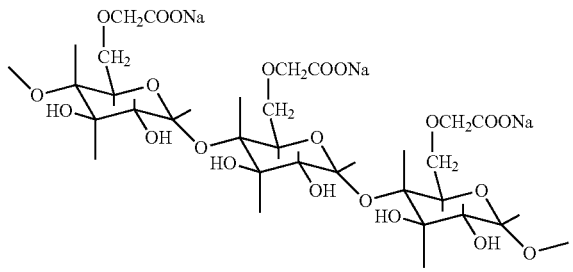

Modified starches such as carboxymethyl starch (CMS) and hydroxyethyl starch are known clinically as plasma substitutes. These modified starches exhibit biocompatibility and safety with no toxic side effects when employed in the human circulatory system. The hemostatic composition, according to the present invention, can further include other plasma substitutes by means of well-known pharmacokinetics approaches and specified physical/chemical properties to produce safe and reliable hemostatic agents.

When cationic starch of the modified starches is selected as a hemostatic material, the surface positive charge of the cationic starch attracts and interacts with electronegative blood erythrocytes, accelerating the blood coagulation process. Furthermore, when contacting blood, the positively charged modified starch adheres tightly to tissue, seals the wound, and rapidly stops bleeding. The cationic starch can be used independently as a hemostatic material or mixed with other modified starches as a composite hemostatic material.

Composite modified starch comprises, but is not limited to, at least pre-gelatinized hydroxypropyl distarch phosphate. Specifically, the hydroxypropyl distarch phosphate is produced by cross-linking and etherifying the starch with propylene oxide and phosphoric acid, followed by pre-gelatinization modification through a spray drying process. The hydroxypropyl distarch phosphate of the present invention has high adhesiveness, strong water absorbency and robust hemostatic effects. It is stable in acidic or alkali environments and can be used as a biocompatible, hemostatic material, a surgical sealant, a tissue healing composition, an anti-adhesion agent, and a tissue repair material.

The cross-linked starch of the present invention includes, but is not limited to, at least one of epichlorohydrin cross-linked starch and cross-linked carboxymethyl starch.

The grafted starches of the present invention include at least a propylene ester-carboxymethyl starch grafted copolymer and a crylic acid-carboxymethyl starch grafted copolymer. Grafted starch has both enhanced water absorption capability and high viscosity/adhesiveness. Therefore, it has a profound effect on hemostasis when applied to wound surfaces, especially combat wounds, traumatic wounds, and profuse bleeding from large arteries and large veins due to aneurysms or large phlebangioma ruptures.

The modified starch, according to the present invention, can be made in powder form, spherical form or aerosol form to be delivered directly to the bleeding wound surface.

As to the wound surface of large burn areas, adopting inhalator or aerosol can stanch blood at the wound surface, reduce tissue fluid exudation, and keep the wound surface moist to aid tissue healing.

In addition, the hemostatic material of the present invention can be made into hemostatic sponge, foam, film, and plaster, which can be applied to a bleeding wound site to stanch blood directly, wherein the hemostatic sponge, foam, the hemostatic film, and the hemostatic plaster can be made into a film or an attaching layer to the inside or surface of a fiber fabric, such as a bandage, band-aid; etc. Such hemostatic sponge, foam, hemostatic film, and hemostatic plaster can be columnar, sheet, massive, flocculent, or membranous.

The modified starch hemostatic foam of the present invention is easy to apply to active bleeding sites and achieves an optimal hemostatic outcome. The hemostatic foam of the present invention can be made from one or more varieties of modified starch processed by vacuum freeze drying. The hemostatic foam of the present invention can be composite hemostatic foam made from one or more varieties of modified starches and other biocompatible hemostatic materials processed by vacuum freeze drying or other drying processes.

Wherein, according to the present invention, other biocompatible hemostatic materials other than the modified starches can comprise one or more of the groups of gelatin, collagen, carboxymethyl cellulose, oxidized cellulose, oxidized regenerated cellulose, and chitosan.

In order to solve the challenge of molding modified starch into sponges and foam, the present invention combines other known bioabsorbable hemostatic materials with strong biocompatibility and clinically acceptable qualities with the modified starch of the present invention to produce composite hemostatic sponges and foams. Whereas other known bioabsorbable hemostatic materials can be of one or more components, the modified starches can also be of one or more components, such as modified starch+gelatin, modified starch+collagen, modified starch+thrombin, modified starch+chitosan, modified starch+carboxymethyl cellulose, and modified starch+hyaluronic acid. These combinations can be molded into sponge and foam forms to satisfy clinical requirements.

Weight proportions between the biocompatible modified starch and other biocompatible hemostatic materials can be 99.9:0.1~1:99.

Specifically, the weight ratio between the modified starch and other biocompatible hemostatic materials preferably is: 95:5, 90:10, 85:15, 80:20, 75:25, 70:30, 65:35, 60:40, 55:45, 50:50, 45:55, 40:60, 35:65, 30:70, 25:75, or 20:80.

This additional coagulant material may be added to the described modified starch hemostatic sponge or foam directly during the vacuum freeze drying production process to produce a composite hemostatic sponge or composite hemostatic foam. The production process may involve, but is not limited to, pre-mixing the coagulant material with the modified starch directly before vacuum freeze drying process.

Accordingly, the coagulant of the present invention comprises one or more combinations of the following group of blood coagulation factors: thrombin, fibrin, calcium agent, polypeptide, peptide, amino acid, and protamine.

The modified starch sponge and foam of the present invention can be manufactured into hemostatic sponges and foam formed by a vacuum freeze drying process utilizing a forming agent or a plasticizing agent.

Whereas the forming agents of the present invention comprises, but not limited to, organic forming agents, inorganic forming agents, natural forming agents, and man-made plasticizing agents, which may include, but not limited to, one or more combinations of glycerol, kaolin, sorbitol, ethanol, ammonia, and polyethylene glycol.

Specifically, the vacuum freeze drying process is a drying method that freezes wet material or solutions to a solid state under low temperatures (−10~−50° C.) and then converts the solid material into a gas and then, in a vacuum (1.3-1.5 Pa), back to a solid material without an intermediate liquid phase (sublimation). As the vacuum freeze drying is processed under low temperature and low pressure, the moisture sublimes directly to produce a substance with numerous special properties. The basic parameters of the vacuum freeze drying process specify both physical parameters and process parameters. The physical parameters include thermal conductivity, transfer coefficient, etc. The process parameters include freezing, heating, state of the material, etc. Continued research on this freezing process involves experiments to identify the optimal freezing curve. As the described biocompatible, modified starch hemostatic material can be made into a hemostatic glue, the physical form can be colloidal, dissolved colloidal, thawed colloidal, semi-liquid or gelatinous, etc. The hemostatic glue can be produced by adding other liquids, not limited to water, to the modified starch by diluting, swelling, or dissolving the liquids in certain proportions.

According to the present invention, the topical application of modified starch can be used as a hemostatic agent to manage and control bleeding wound surfaces in humans, mammals, birds, or reptiles, and the internal application for hemostasis of bleeding wound surfaces within human bodies, tissues and organs following surgical operations and trauma treatments, under open surgery or nasoscope, laryngoscope, endoscope and laparoscope.

The modified starch hemostatic composition, according to the present invention, can be applied for hemostasis on bleeding bone tissue caused by surgery or trauma, particularly for hemostasis in spongy bone tissue. In thoracic or neurological operations involving some patients, such as children, elderly people, and patients with osteoporosis, sternal bleeding and skull bleeding is difficult to control. It is common to apply bonewax to the sternum or skull, however, bonewax is slow to absorb and may cause complications such as non-union or infection. The modified starch composition, according to the present invention, is a biocompatible substitute for bonewax to control bone bleeding and mechanically seal the wound caused by surgery or trauma with its robust hydrophilic properties, strong adhesiveness and ease of molding. The modified starch hemostatic material degrades rapidly after surgery and avoids the complicating issues of non-union and infection associated with bonewax. When the modified starch is applied as a hemostatic material, other biological benefits of the described modified starch are worthy of attention. It is essential to evaluate the described modified starch composition as having further positive effects on wound inflammation, tissue adhesion and tissue healing while acting as a hemostat.

It is proven that the modified starch hemostatic material, according to the present invention, has further application as an absorbable, postoperative tissue adhesion barrier. The adhesion barrier of the modified starch, according to the present invention, prevents wounded tissue or organs from adhering to other tissue or organs in the vicinity, thereby reducing local bleeding and exudation, by mechanically isolating the wound or wound surface from adjacent tissue and surrounding organs, such as the peritoneum.

The modified starch, according to the present invention, can promote tissue healing, including skin, subcutaneous soft tissue, musculature, bone tissue, neurological tissue, nerve tissue, and wounded tissue of the liver, kidney, spleen, etc., through proper dosage and application. The modified starch can be a "scaffold" for skin tissue cells to promote healing and the growth of skin tissue from large wound surfaces due to burns, a "scaffold" for osteocyte growth and propagation in bone defects from trauma, bone tumor resection, etc., and a "scaffold" for neurological tissue cell growth and propagation when applied to injured neurological tissue caused by brain trauma, brain tumor resection, etc. The modified starch, according to the present invention, has further applications as a biocompatible surgical sealant, capable of forming a protective layer of colloid or film on the wound surface to seal and prevent drainage of blood, tissue fluids, lymph fluid, cerebrospinal fluid, bile, gastric fluid, and other intestinal fluids resulting from surgery and trauma treatment. This sealing effect will prevent lymph fistula leakage, bile flaccidity, pleural flaccidity, intestinal flaccidity, cerebrospinal flaccidity, and vascular flaccidity.

The modified starch, according to the present invention, has further application as a biocompatible tissue adhesive, capable of adhering, repairing, and bonding wounded nerve tissue, musculature, and tissues of the bone, skin, viscera, and subcutaneous tissue. It can also bond other curative materials to wounded tissue and organs for tissue repair.

In addition to the above advantages, the modified starch of the present invention has a bacteriostatic and anti-inflammatory effect on bleeding wound surfaces. The modified starch hemostatic material, according to the present invention, has a hemostatic effect which controls bleeding, reduces blood and tissue fluid exudation, and maintains a moist wound surface. As a result, it suppresses the growth of bacteria and reduces the inflammatory response, diminishing local irritation and relieving pain. Furthermore, to strengthen the anti-inflammatory response, known antibiotic or other anti-pyrotic agents can be added to the modified starch during the manufacturing process to produce hemostatic powder, sponges and foams, hemostatic glues and gels, etc., all of which are suitable for topical and internal clinical applications.

Another advantage of the modified starch hemostatic material of the present invention is the rapid particle dissolution in water, facilitating the easy removal of excess modified starch particles from the wound by simple saline irrigation. The residual modified starch not actively involved in hemostasis can be rinsed away by irrigation. In the treatment of battle wounds, self rescue, or first aid, the hemostatic material remaining in small amounts will be absorbed by the body and the irritation of wound debridement or gauze removal is avoided.

The modified starch hemostatic material has properties of stability, extended shelf life, resistance to high and low pressure, resistance to high temperature (up to 60° C.) and low temperature (down to −40° C.), convenient storage, and physical stability. Therefore, it may also be employed as a hemostatic material for the military, emergency, and first-aid uses. Particularly, it can be adapted for extreme environmental conditions such as desert areas, polar regions, alpine areas, outer space, and underwater probes.

The modified starch sponge and foam has physical properties of pliability, flexibility, moldability, and curling. It can be adapted for wound surfaces with various shapes, sizes, and features, such as deep and irregular anatomical wounds, organ physiologies, both inside and outside the lacuna surface, and applied under endoscope, laparoscope or open surgery.

To enhance the safety of applying the modified starch to wound surfaces, tissue, etc., the modified starch material, according to the present invention, can be packaged and sterilized with, but not limited to, gamma irradiation, oxirane, and ozone sterilization.

At least a production process of a biocompatible modified starch material according to the present invention, comprising the steps of:

providing a modified hygroscopic biocompatible starch material and adding into a agglomerator under 40~50° C.; and adding distilled water and producing a modified starch finished product material by particle agglomerating and pellet processing;

wherein the modified starch finished product has a molecular weight over 15,000 Daltons (for instance, 15,000~2,000,000 Daltons) and a grain diameter of 10~1000 μm, wherein starch grains with diameters of 30~500 μm represent no less than 95% of the total amount of starch grains, wherein the modified starch finished product can provide effects of hemostasis, adhesion prevention, tissue healing promotion, sealing, adhesive plugging, bonding to a bleeding wound surface, and bacteriostatic and anti-inflammatory effect on the bleeding wound surface of either external or internal bleeding tissue and organs. The modified starch finished product can be applied for topical use, for surgical use, or via laryngoscope, endoscope and laparoscope.

BRIEF DESCRIPTION OF THE DRAWINGS

FIG. 12 illustrates a comparison of water absorption ability between carboxymethyl starch 66# and Arista™.

FIG. 13 illustrates a comparison of work of adhesion among carboxymethyl starch 66#, hydroxyethyl starch 88#, and Arista™.

FIG. 14 illustrates a comparison of viscosity between carboxymethyl starch 66#, according to the present invention, and Arista™.

FIG. 15 illustrates water absorbency of various modified starch by the method of centrifugation.

FIG. 16 illustrates hemostatic effects of the materials on experimental animals under different hemostatic conditions.

FIG. 17 illustrates grades of intestinal adhesion in different rat groups.

FIG. 18 illustrates results of seven bone healing indexes in rabbit groups.

FIG. 19 illustrates a comparison of physical and chemical properties among the above-mentioned hemostatic sponges and other hemostatic sponges FIG. 20 illustrates water absorption ability of composite hemostatic sponges.

FIG. 21 shows a comparison of water absorbency between composite hemostatic sponges and other hemostatic sponges.

DETAILED DESCRIPTION OF THE PREFERRED EMBODIMENT

Figure 1:
FIG. 1 illustrates hemostatic effects of Arista™ in a rabbit liver bleeding model.

The present invention provides a modified starch material with the biocompatible properties of hemostasis, adhesion prevention, tissue healing, absorbable tissue sealing and tissue bonding. More specifically, the modified starch material, which is rapidly degraded by humans and animals when applied directly to the wound surface of humans and mammals, including a bleeding or exudating wound surface, is able to stop bleeding, prevent adhesions, promote tissue healing, seal wounded tissue, prevent bleeding and fluid exudation from tissue, bond and repair tissue or organs injured during trauma or surgery, and avoid or minimize surgical sutures.

Starch is a glucosan. At room temperature, raw starch is generally not soluble in water, nor does it readily absorb water. Raw starch normally absorbs water at temperatures above 60° C. and swells to an adhesive, translucent and colloidal solution. The modified starch is raw starch processed through physical and chemical modifications, resulting in physical and chemical changes which make its characteristics and properties suitable for applications in various industries. Starch is generally classified by its origin, such as potato starch or corn starch, etc. There are two types of glucose chains in starch, including a simple chain called amylose and a complex branched form called amylopectin. The diameter range of starch grains is normally between 1~100 μm and the average diameter is from 15 to 30 μm.

Natural raw starch has minimal hemostatic characteristics because starch grains are small and light and the hydrophilic properties are unsatisfactory at room temperature.

The modified starch acquires certain chemical and physical characteristics by cutting, rearranging, or adding other chemical groups that change the structure of the raw starch molecular chain. The modified starch can be categorized primarily into physically modified starch, chemically modified starch, enzymatically modified starch, and naturally modified starch, according to the performed modification process.

Physical modification is the process which produces modified starch, with the desired properties and functions, by physically changing the microcrystalline starch structure through heating, extrusion, and irradiation. Specifically, physically modified starch includes of pre-gelatinized starch (α-starch), γ-ray, microwave or high frequency radiation starch, mechanically milled starch, and steam treated starch, etc.

Chemically modified starch is produced by processing the raw starch with chemical agents and changing the molecular structure to achieve the desired modified starch properties. Specifically, the chemically modified starch is categorized primarily as acid modified starch, oxidized starch, baking dextrin, esterified starch, etherified starch, grafting starch, etc.

Enzymatically modified starch is produced by processing the raw starch with enzymes, such as α-cyclic dextrin, β-cyclic dextrin, γ-cyclic dextrin, malto-dextrin and amylopectin.

Naturally modified starch may possess the same properties as chemically modified starch by changing the structure of natural raw starch with a variety breeding and genetic techniques.

The modified starches generally require multi-modification of the raw starch to achieve the desired properties. In another words, it is the modification with two or more modifying methods that produces the final, composite, modified starch. Most of the widely used modified starches are composite modified starches that have been modified several times.

The modified starch material according to the present invention can be applied to a bleeding wound surface in humans and animals as a hemostatic agent for topical and surgical use. The modified starch material according to the present invention can be used on soft tissue and organs to rapidly and effectively control bleeding.

The present invention provides methods and technological approaches of producing the hemostatic modified starch material, which produce the modified starch in form of powder, sponge, foam, colloid, film, and other forms that satisfy various surgical hemostatic requirements, including ease of use.

The present invention provides biocompatible modified starch material which can be produced by various methods and processes to achieve essential physical and chemical properties, characteristics, technical parameters, and technical indices required for hemostasis, adhesion prevention, sealing, adhesive gluing, promotion of healing, and tissue bonding within the application environment. The modified starch hemostatic material is safe, reliable, absorbable, and rapidly degradable by humans and animals.

Additionally, the modified starch material of the present invention can be used as a biocompatible anti-adhesion agent, a tissue healing promotion material, a surgical sealant, and a tissue bonding composition for tissue repair.

The technical formulas of the present invention fulfill the foregoing performance requirements with modified starch applications as a biocompatible hemostatic material with characteristics that include dissolving or swelling in water and the subsequent formation of an adhesive glue or adhesive gel.

The characteristics of the modified starch of the present invention further include the acquisition of hydrophilic groups in its molecular chains through the described modification process.

When the hydrophilic and enhanced adhesive modified starch is applied to bleeding wound sites, it rapidly absorbs water in the blood and concentrates blood components. Concurrently, this interaction creates an adhesive matrix formed with the blood and plasma which adheres to the bleeding wound, mechanically seals broken blood vessels and stops bleeding.

The modified starch material according to the present invention includes starch modified physically, chemically, naturally, or enzymatically, and starch modified repeatedly with at least one of the above methods or a combination of two or more of the above methods.

The physical modifying process according to the present invention employs irradiation, mechanical, and steam modification.

Physically modified starch, for example, a pre-gelatinized starch treated solely with spray drying or irradiation process, is remarkably safe as a bio-absorbable, hemostatic material since it is not treated with any chemical agents.

Pre-gelatinized starch can be modified by an extrusion process, roller drying, and a spray drying process.

Specifically, after heating the raw starch with a measured amount of water, starch granules swell to a pasty substance, regularly arranged micelle of starch are broken, crystallites disappear, and the resulting composition is easily degraded under the process of amylase. Pre-gelatinized starch is able to swell and/or dissolve in cold or room temperature water and form an adhesive paste whose retrogradation is lower than that of raw starch, affording easier handling during the production process. Raw starch can be pre-gelatinized through solely a physical modification process without adding any chemical agents and becomes a hemostatic material with enhanced hydrophilic and adhesive properties.

The pre-gelatinized starch of the invention is safe, non-toxic, and has no adverse side effects. The pre-gelatinized starch is readily degraded and metabolized by enzymes in the body. The described pre-gelatinized material is safe and biocompatible.

The chemical modifying as described above includes acidolysis, oxidation, esterification, etherification, cross-linking, chemical agent grafting. Alternatively, multiple modifying processes comprise at least two of the above processes, or one of the above modifying processes performed at least twice.

According to the present invention, by adding the functional group on the raw starch glucose units with chemical agents, e.g. by carboxylation modification, or hydroxylation modification, the starch captures hydrophilic groups in its molecular structure and obtains hydrophilic properties. By using bifunctional or polyfunctional chemical agents to cross-link the raw starch macromolecules or grafting external macromolecurlar hydrophilic groups to the raw starch, the starch acquires enhanced hydrophilic properties and viscosity/adhesiveness in a water solution. The viscosity of modified starch relates to the raw starch origin and the degree of substitution of external and the cross-linked or grafted functional groups, etc. When contacting blood, the hydrophic and adhesive properties of the prescribed modified starch will produce a "starch-blood coagulation matrix" with strong adhesive characteristics which can seal wounded tissue and stop bleeding. In addition, the interaction between the formed blood coagulation matrix and the functional groups of tissue proteins will cause the "starch-blood coagulation matrix" to adhere to and seal the wounded tissue, resulting in hemostasis.

An advantage of the present invention is that the modified starch compositions are easily swollen and/or dissolved in water, allowing the formed adhesive gel at the wound site to be irrigated and dissolved by normal saline rinse after hemostasis. Since the residual modified starch particles not in contact with blood can be easily washed away with water, absorbed by an aspirator, or wiped away with gauze materials, it will minimize the residual particles in the wound and the risk of tissue inflammation.

Specifically, the modified starch of the present invention contains one or more groups of pre-gelatinized starch, acid modified starch, dextrin, oxidized starch, esterified starch, etherified starch, or cross-linked starch.

The hemostatic composition of the present invention comprises two or more modified starches to satisfy the physical and chemical properties of a hemostatic agent, where the weight ratio of the two modified starch groups can be 99:1~1:99.

Specifically, the weight ratio of the two modified starch groups can be: 95:5, 90:10, 85:15, 80:20, 75:25, 70:30, 65:35, 60:40, 55:45, or 50:50.

The main physical parameters of the modified starch, according to the present invention, are provided below:

The modified starch of the present invention has a molecular weight over 15,000 Daltons (for instance, 15,000~5,000,000 Daltons).

The modified starch of the present invention has a water absorbency capacity not lower than one time its weight (i.e. 1 gram of described modified starch can absorb 1 gram or more of water); whereas it can be 1~500 times generally and 2~100 times preferably.

The modified starch composition of the present invention comprises, but is not limited to, at least one carboxymethyl starch, hydroxyethyl starch, and cationic starch.

For example, the carboxymethyl starch is a polymer of linear structure as expressed in the following formula:

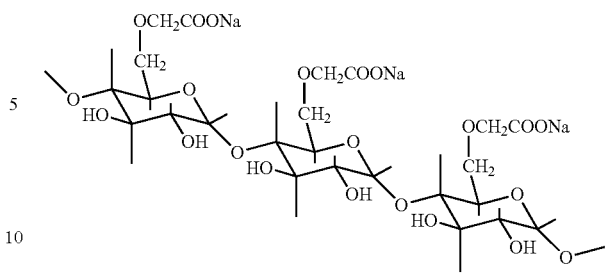

The modified starches such as carboxymethyl starch (CMS) and hydroxyethyl starch are known clinically as plasma substitutes. These modified starches exhibit biocompatibility and safety with no toxic side effects when employed in the human circulatory system. The hemostatic composition, according to the present invention, can also include other plasma substitutes by means of well-known pharmacokinetics approaches and specified physical/chemical properties to produce safe and reliable hemostatic agents.

When cationic starch of the modified starches is used as a hemostatic material, the surface positive charge of the cationic starch can attract and interact with electronegative blood erythrocytes, accelerating the blood coagulation process. Furthermore, when contacting blood, the positively charged modified starch adheres tightly to tissue, seals the wound, and rapidly stops bleeding. The cationic starch can be used independently as a hemostatic material, or mixed with other modified starches as a composite hemostatic material.

The composite modified starch comprises, but not limited to, at least pre-gelatinized hydroxypropyl distarch phosphate. Specifically, the hydroxypropyl distarch phosphate is produced by cross-linking and etherifying the starch with propylene oxide and phosphoric acid, followed by pre-gelatinization modification through a spray drying process. The hydroxypropyl distarch phosphate has high adhesiveness, strong water absorbency and robust hemostatic effects. It is stable in acidic or alkali environments and can be used as a biocompatible, hemostatic material, a surgical sealant, a tissue healing composition, an anti-adhesion agent, and a tissue repair material.

The cross-linked starch of the present invention comprises, but is not limited to, at least one epichlorohydrin cross-linked starch and one cross-linked carboxymethyl starch.

The grafted starches of the present invention comprise at least a propylene ester-carboxymethyl starch grafted copolymer and a crylic acid-carboxymethyl starch grafted copolymer. Grafted starch has both enhanced water absorption capability and high viscosity/adhesiveness. Accordingly, it has a profound effect on hemostasis when applied to wound surfaces, especially combat wounds, traumatic wounds, and profuse bleeding from large arteries and large veins due to aneurysms or large phlebangioma ruptures.

The modified starch, according to the present invention, can be made into powder form, spherical form or aerosol form to be delivered directly to the bleeding wound surface.

For large wound surfaces from burns, selecting an aerosol sprayed modified starch hemostatic powder in combination with a modified starch sponge or film can achieve not only hemostasis but also reduce tissue fluid exudation. This combined application preserves a moist wound surface and develops a "scaffold" for fiber cell growth and propagation through the healing tissue.

Specifically, the hemostatic powder of the present invention is made by an agglomeration process and pellet fabrication. Normally, modified starch grain dimensions are relatively small and light and may need to agglomerate into larger sizes and heavier weights which can readily disperse into the excess blood and generate coagulation close to the broken vessels to achieve an optimal hemostatic outcome. The agglomeration process may not be necessary for large sized modified starch particles such as grafted starch or cross-linked starch.

The modified starch particles of the present invention have a diameter range of 10~1000 μm, preferably 30~500 μm. Starch particles with diameters of 30~500 μm represent no less than 95% of the total starch particles in the preferred embodiment. The measured, optical diameter of the starch particles is between 50~250 μm.

Specifically, because pre-agglomerated modified starch particles are small and lightweight, they readily form a colloid on the particle surface with the moisture in blood. In this case, it affects the hemostatic outcome by preventing water molecules from further dispersing to other starch particles. The present invention accepts and adopts agglomeration processing technologies in the food and pharmaceutical industries to accumulate microscopic modified starch particles in the general 5~50 μm diameter range, creating clinically applicable particles with a diameter range of 30~500 μm. Modified starch particles produced by the process disclosed above exhibit rapid water absorption, strong hydrophilic properties and rapid dispersion in blood to achieve improved hemostatic outcomes, while not readily forming a colloidal protecting layer which may disrupt the hemostatic effect.

To fulfill the requirements of clinical operations, the present invention provides various methods and processes to produce hemostatic compositions with acceptable properties that assist doctors with hemostatic therapy during surgery. The powder form modified starch hemostat readily adapts to diffuse oozing of blood on large surface areas, and the hemostatic powder can be delivered to a bleeding wound surface under celioscope, nasoscope, laparoscope or endoscope. The powder will have a sealing effect on postoperative biliary fistulas, thoracic cavity fistulas, lymph fistulas, intestinal fistulas, and wound tissue exudation. Excess, residual powder can be rinsed away with normal saline to reduce the risk of inflammation and infection.

The hemostatic material of the present invention can be a hemostatic sponge, a hemostatic foam, a hemostatic film, or a hemostatic bandage, which can be applied directly to a wound surface to stop bleeding, wherein the hemostatic sponge/foam, the hemostatic film, and the hemostatic bandage can be made into a pad or patch by attaching a backing layer or substrate of fiber fabric.

The hemostatic sponge, hemostatic foam, hemostatic film, and hemostatic bandage according to the present invention can be produced into, but not limited to, the following forms: columnar, sheet, flocculent, or membranous.

Concerning active bleeding and high pressure arterial bleeding, surgeons or emergency responders must apply pressure to the wound to stop bleeding. In this circumstance, the hemostatic powder and the clot formed can be easily washed away by the high pressure blood flow resulting in a failure of hemostasis. In addition, by compressing the hemostatic powder on the bleeding wound, the clotting action forms an adhesive gel which easily sticks and adheres to surgical gloves, instruments, and gauze. As a result, upon removal of gloves, instruments or gauze from the coagulated wound, re-bleeding may occur. The present invention provides a modified starch sponge or foam which can be applied and remain directly on the wound, thereby solving the above problem of re-bleeding. The modified starch hemostatic sponge or foam is absorbable, easy to use and may remain directly on the wound for a satisfactory effect.

The hemostatic sponge and foam of the present invention can be made from one or more, but not limited to, modified starch processes such as vacuum freeze drying.

The hemostatic sponge and foam of the present invention can be a composite hemostatic sponge and composite hemostatic foam made from one or more compositions of modified starch and other biocompatible hemostatic materials through, but not limited to, the vacuum freeze drying process.

Whereas, the biocompatible hemostatic materials described above comprise, but not limited to, one or more groups of gelatin, thrombin, collagen, carboxymethyl cellulose, oxidized cellulose, oxidized regenerated cellulose, chitosan, or sodium alginate.

To solve the challenge of molding modified starch into sponges and foam, the present invention combines other known bio-absorbable hemostatic materials with strong biocompatibility and clinically acceptable qualities with the modified starch to produce composite hemostatic sponges and foams. Whereas other known bioabsorbable hemostatic materials can be of one or more components, modified starches can also comprise one or more components, such as modified starch+gelatin, modified starch+collagen, modified starch+thrombin, modified starch+chitosan, modified starch+carboxymethyl cellulose, and modified starch+hyaluronic acid. These combinations can be molded into sponge and foam form to satisfy clinical requirements.

Weight proportion between the biocompatible modified starch and other biocompatible hemostatic materials can be 99.9:0.1~1:99.

Specifically, the weight ratio between the modified starch and other biocompatible hemostatic materials can preferably be: 95:5, 90:10, 85:15, 80:20, 75:25, 70:30, 65:35, 60:40, 55:45, 50:50, 45:55, 40:60, 35:65, 30:70, 25:75, or 20:80.

This additional coagulant material can be added to the modified starch hemostatic sponge or foam of the present invention directly during the vacuum freeze drying production process to produce a composite hemostatic sponge or composite hemostatic foam. The production process can, but not limited to, pre-mixing the coagulant material with the modified starch directly before vacuum freeze drying process.

Whereas the coagulant of the present invention comprises, but not limited to, one or more combinations of the following blood coagulation factors: thrombin, fibrin, calcium agent, polypeptide, peptide, amino acid, and protamine.

The modified starch sponge and foam of the present invention can be manufactured into hemostatic sponge and foam form by a vacuum freeze drying process utilizing a forming agent or a plasticizing agent.

Whereas the forming agents as described above comprise, but not limited to, organic forming agents, inorganic forming agents, natural forming agents, and man-made plasticizing agents, which can include, but not limited to, one or more combinations of glycerol, kaolin, sorbitol, ethanol, ammonia, and polyethylene glycol.

Specifically, vacuum freeze drying process is a drying method that freezes wet material or solutions to a solid state under low temperatures (−10~−50° C.) and then converts the solid material into a gas and then, in a vacuum (1.3-1.5 Pa), back to a solid material without an intermediate liquid phase (sublimination). As the vacuum freeze drying is processed under low temperature and low pressure, the moisture sublimes directly to produce a substance with numerous special properties.

The basic parameters of the vacuum freeze drying process specify both physical parameters and process parameters. The physical parameters include thermal conductivity, transfer coefficient, etc. The process parameters include freezing, heating, state of the material, etc. Continued research on this freezing process involves experiments to identify the optimal freezing curve.

As the described biocompatible, modified starch hemostatic material can be made into a hemostatic glue, the physical form can be colloidal, dissolved colloidal, thawed colloidal, semi-liquid or gelatinous, etc.

The hemostatic glue can be produced by adding other liquids, not limited to water, to the modified starch by diluting, swelling, or dissolving the liquids in certain proportions.

The present invention discloses the topical application of modified starch as a hemostatic agent to manage and control bleeding wound surfaces in humans, mammals, birds, or reptiles, and the internal application for hemostasis of bleeding wound surfaces within human bodies, tissues and organs following surgical operations and trauma treatments, under open surgery or nasoscope, laryngoscope, endoscope and laparoscope.

It is important to note that the modified starch hemostatic composition, according to the present invention, can be applied for hemostasis on bleeding bone tissue caused by surgery or trauma, particularly for hemostasis in spongy bone tissue. In thoracic or neurological operations involving some patients, such as children, elderly people, and patients with osteoporosis, sternal bleeding and skull bleeding is difficult to control. It is common to apply bonewax to the sternum or skull, however, bonewax is slow to absorb and may cause complications such as non-union or infection. The modified starch composition, according to the present invention, is a biocompatible substitute for bonewax to control bone bleeding and mechanically seal the wound caused by surgery or trauma with robust hydrophilic properties, strong adhesiveness and ease of molding. The modified starch hemostatic material degrades rapidly after surgery and avoids the complicating issues of non-union and infection associated with bonewax.

As the modified starch is applied as hemostatic material, other biological benefits of the modified starch are worthy of attention. It is essential to evaluate the modified starch composition for its positive, additional effects on wound inflammation, tissue adhesion and tissue healing while it functions as a hemostat.

Through research and experimentation, it is proven this modified starch hemostatic material, according to the present invention, has further application as an absorbable, postoperative tissue adhesion barrier. The adhesion barrier of the modified starch, according to the present invention, prevents wounded tissue or organs from adhering to other tissue or organs in the vicinity, thereby reducing local bleeding and exudation, by mechanically isolating the wound or wound surface from adjacent tissue and surrounding organs, such as the peritoneum.

The modified starch, according to the present invention, can promote tissue healing, including skin, subcutaneous soft tissue, musculature, bone tissue, neurological tissue, nerve tissue, and wounded tissue of the liver, kidney, spleen, etc. through proper dosage and application. The modified starch can create a "scaffold" for skin tissue cell healing and growth of skin tissue from large wound surfaces due to burns, and a "scaffold" for osteocyte growth and propagation in bone defects from trauma, bone tumor resection, etc.; and a "scaffold" for neurological tissue cell growth and propagation when applied to injured neurological tissue caused by brain trauma, brain tumor resection, etc.

The mechanism for promoting tissue healing is the "glue" formation after modified starch contacts blood and establishes the "scaffold" on the wound surface which facilitates the adherence, growth, connection and propagation of tissue cells such as osteoblasts or fibroblasts. In addition, local blood platelets are increasingly concentrated on the wound and, when activated, release tissue factors which promote healing.

The modified starch, according to the present invention, has further applications as a biocompatible surgical sealant, capable of forming a protective layer of colloid or film on the wound surface to seal and prevent drainage of blood, tissue fluids, lymph fluid, cerebrospinal fluid, bile, gastric fluid, or and other intestinal fluids resulting from surgery and trauma treatment. This sealing effect will prevent lymph fistula leakage, bile flaccidity, pleural flaccidity, intestinal flaccidity, cerebrospinal flaccidity, and vascular flaccidity.

The modified starch, according to the present invention, has further applications as a biocompatible tissue adhesive, capable of adhering, repairing, and bonding wounded nerve tissue, musculature, and tissues of the bone, skin, viscera, and subcutaneous tissue. It will also bond other curative materials to wounded tissue and organs.

The differences between the present invention and prior hemostatic materials are:

In contrast, the microporous polysaccharide hemospheres of U.S. Pat. No. 6,060,461, an absorbable, biocompatible hemostatic material, are formed by cross-linking starch with epichlorohydrin. The mechanism of the microporous polysaccharide hemospheres involves the molecular sieving of blood components based on their molecular weight. This microporous hemostat allows water molecules and other lower weight molecules into its particles and concentrates heavier molecules, such as erythrocytes, platelets, and fibrinogen, on the surface of the particles to promote blood coagulation.

The microporous polysaccharide hemospheres of U.S. Pat. No. 6,060,461 are produced under a proprietary process not disclosed in the patent. However, normal modified starches, including cross-linked modified starch, do not necessarily possess the microporous structure of the microporous polysaccharide hemospheres as described in U.S. Pat. No. 6,060,461. By contrast, the present invention does not employ the microporous properties of a molecular sieve in modified starch to achieve hemostasis. Rather, the present invention adopts other technical processes to import hydrophilic groups to raw starch molecules which enable the modified starch to directly interact with water molecules under hydration, resulting in rapid dehydration of blood and concentration of blood clotting components. This action does not relate to whether or not the modified starch has a microporous surface.

In addition, by means of changing the degree of substitution, selecting proportional ratios of amylopectin and amylose, adding functional groups to starch molecular or modifying the functional groups in starch chains, etc., the present invention is able to increase the hydrophilic property and viscosity of the modified starch, which produces an "adhesive gel" that adheres strongly to tissue and mechanically seals broken blood vessels after contact with blood. The above properties were not identified in the microporous polysaccharide hemospheres of U.S. Pat. No. 6,060,461 and these described properties in present invention have advantages over prior hemostatic materials. The modified starch in this invention can be made into hemostatic powder, hemostatic sponges and foam, hemostatic glue and gel, independent of whether or not the modified starch has a microporous structure on the surface. On the contrary, the hemostatic effect of the powder, the sponge, the foam, the glue and the gel relates to the induced physical and chemical properties of the modified starch under which the invention is synthesized.

When compared with Chinese publication patent number CN1533751A, hemostatic dressings consist of two necessary components: fabric and a multi-porous polymer substrate attached to the fabric, which then forms a composite structure. The fabric is made from the oxidized regenerated cellulose described previously. Since human physiology lacks sufficient degrading enzymes for oxidized regenerated cellulose, this hemostatic material is slow to absorb in the human body, thus risking local infections and compromising tissue healing In the description of the substrate, the patent identifies dextran and carboxymethyl cellulose as derivatives of dextran. Cellulose and starch are two large classes of dextran with distinctly different properties, though both are polysaccharide dehydrating and poly-condensing from glucose monomers. Firstly, the polymerization degree of starch is generally from hundreds to thousands, and the molecular weight of starch is from tens of thousands of Daltons to hundreds of thousands of Daltons. The polymerization degree of cellulose is generally thousands and the molecular weight of cellulose is from hundreds of thousands of Daltons to millions of Daltons. Secondly, all repeating glucose chains in starch are arranged in the same direction, while repeating cellulose chains connect to each other by rotating 180° along the axial direction, which produces the different glucose and cellulose structures. Further, starch is easily degraded and metabolized by amylase and carbohydrase, enzymes abundant in the human body. Conversely, cellulose is slow to metabolize and absorb since the human body lacks sufficient amounts of the requisite degrading enzymes.

Consequently, when producing biocompatible, absorbable materials employed for hemostasis, the properties of starch are superior to those of cellulose since modified starch is readily degraded into glucose by the abundant amount of amylase in the human body and absorbed rapidly. The biocompatibility advantage of starch over cellulose is apparent. Furthermore, the oxidized regenerated cellulose dressing has weak adhesion to tissue, requires compression to maintain contact with tissue, and therefore cannot effectively seal blood vessels in the wounded surface, limiting its clinical applications.

In addition to the above different properties, the modified starch described in the present invention has a bacterio-static and anti-inflammatory effect on bleeding wound surfaces. The modified starch hemostatic material, according to the present invention, has a hemostatic effect which controls bleeding, reduces blood and tissue fluid exudation, and maintains a moist wound surface. As a result, it suppresses the growth of bacteria and reduces the inflammatory response, diminishing local irritation and relieving pain. Furthermore, to strengthen the anti-inflammatory response, known antibiotic or other anti-pyrotic agents can be added to the modified starch during the manufacturing process to produce hemostatic powder, sponges and foams, hemostatic glues and gels, etc., all of which are suitable for topical and internal clinical applications.

Another advantage of the modified starch hemostatic material according to the present invention is the rapid particle dissolution in water, facilitating the easy removal of excess modified starch particles from the wound by simple saline irrigation. The residual modified starch not actively involved in hemostasis can be rinsed away by irrigation. In the treatment of battle wounds, self rescue, or first aid, the hemostatic material remaining in small amounts will be absorbed by the body and the irritation wound debridement or gauze removal is avoided.

The modified hemostatic starch material has properties of stability, extended shelf life, resistance to high and low pressure, resistance to high (up to 60° C.) and low (down to −40° C.) temperatures, storage convenience, and physical stability. Therefore, it can be employed as a hemostatic material for military, emergency, and first-aid uses. Particularly, it can be adapted in extreme environmental conditions such as desert areas, polar regions, alpine areas, outer space, and underwater probes. The modified starch sponge has the physical properties of pliability, flexibility, moldability, and curling. It can be adapted for wound surfaces with various shapes, sizes, and features, such as deep and irregular anatomical wounds and organs, both inside and outside the lacuna surfaces, and may be applied via endoscope, laparoscope or open surgery.

To enhance the safety of applying the modified starch to wound surfaces, tissue, etc., the modified starch material, according to the present invention, can be packaged and sterilized with, but not limited to, gamma irradiation, oxirane, and ozone sterilization.

However, adopting alcohol sterilization, autoclave or steam sterilization is not recommended as it may change the physical and chemical properties of the modified starch and compromise its hemostatic effect.

A. Preparation of Modified Starch Powder

Preferred Embodiment 1

A biocompatible modified starch material uses as hemostatic material. It includes carboxymethyl starch (66#). Carboxymethyl starch material is added into an agglomerator at 40~50° C. Distilled water is added. The processes include particles coagulation (agglomeration) and pellet making. Molecule weight of the carboxymethyl starch (66#) is 15,000~2,000,000 Dalton. Diameter of the particles is 10~1000 μm. Particle diameter is between 30 and 500 μm in no less than 95% of the particles. Viscosity of a 6.67% suspension at 37° C. is 557.9 mPa·s. Work of adhesion under room temperature is 68.1 g·sec when the modified starch is saturated with water.

Preferred Embodiment 2

A modified starch absorbable hemostatic material includes hydroxyethyl starch (88#). Hydroxyethyl starch material and distilled water are added into an agglomerator 40~50° C. The processes include particles coagulation (agglomeration) and pellet making Molecule weight of the hydroxyethyl starch (88#) is 15,000~1,000,000 Dalton. Diameter of hydroxyethyl starch (88#) particles is 10~1000 μm. Particle diameter is between 50 and 500 μm in no less than 95% of the particles. Work of adhesion under room temperature is 420.9 g·sec when the modified starch is saturated with water.

The water absorption ability of this invention is measured by a capillary method. Water is added into an acid burette so that the liquid level at zero graduation of the acid burette equals to the bottom of the filter plate of a sand core funnel. Filter paper is trimmed into a disc with a 2.25 cm radius, weighed, and put into the sand core funnel until it fully touches the filter plate. The piston is opened until the filter paper is fully absorbed with water. The acid burette is adjusted to zero graduation. 0.1 g sample powder is weighed, scattered evenly on the filter paper, and placed in the sand core funnel. Starting from the time when liquid begins to fall, liquid level is recorded every 20 s, 40 s and 60 s. Water absorption speed and water absorption saturation per unit time are calculated.

A comparison of water absorption ability between carboxymethyl starch 66# and Arista™ groups is illustrated in Table 1.

As illustrated in Table 1, the water absorption speed of carboxymethyl starch 66# within all three 20 s intervals are greater than that of Arista™, indicating that 66# absorbs water faster than Arista™ and is more effective. The capacity of water absorption of 66# is almost 5 times as that of Arista™ in the first 20 s interval.

The water absorption speed refers to the average water absorption speed in the first 20 s, the second 20 s, and the third 30 s intervals. V20 s=water absorbed in 20 s(ml)/20 (s).

Saturation rate of water absorption refers to the amount of water absorbed by the sample in a certain period of time divided by its maximal water absorption capacity (i.e. the absolute value of water absorbency). This measure reflects the water absorption speed of the same sample from another angle.

As illustrated in Table 1, 66# has a higher saturation rate of water absorption than Arista™ at the 20 s, 40 s, and 60 s intervals, indicating that 66# absorbs more water than Arista™ in a same period of time. For 66#, 58 percent of total water absorbency is achieved in 20 s; nearly 95% is achieved in one minute. The water absorption speed of 66# is greater than that of Arista™.

The stickiness of the present invention is measured as the work of adhesion using a texture analyzer (physical property analyzer; Stable Micro System, Model TA-XT plus). Probes used in the experiment includes A/BE (backward extrusion probe) and P36R (cylindrical probe).

Experiment conditions are: pre-experimental speed: 0.5 mm/sec; experimental speed: 10.0 mm/sec; stress: 100 g; retrieval distance: 5.0 mm; contact time: 10.0 sec; trigger: automatic, 5 g.

A comparison of work of adhesion among carboxymethyl starch 66# (according to the present invention), hydroxyethyl starch 88#, and Arista™ is illustrated in Table 2.

When the probe moves back, it will encounter the adhesive force produced by the sample. For the probe to separate completely from the sample, it must do work. The work done during this period is referred to as the work of adhesion and can be used to measure the adhesive strength (degree of firmness) between the adhesive agent and probe surface.

25% saturation rate refers to the saturation at ¼ maximal water absorption capacity.

50% saturation rate refers to the saturation at ½ maximal water absorption capacity.

100% saturation rate refers to the saturation at maximal water absorption ability.

As illustrated in table 2, the adhesiveness (stickiness) of Arista™ is much lower than that of 66# and 88#. The work of adhesion of 88# decreases with increasing saturation rate, and has particularly high adhesiveness (stickiness) and at lower saturation rate. Adhesiveness (stickiness) of 66# increases gradually. At maximal saturation, both materials have significantly higher stickiness than Arista™, and produce better effects of adhesive plugging.

Viscosity of the present invention is measured by a viscometer (brookfiled Dv-2). Test conditions are: Rotor 3; rotating speed: 60; concentration of modified starch solution: 6.67%; temperature: 37° C.

A comparison of viscosity between carboxymethyl starch 66# in the present invention and Arista™ is illustrated in Table 3.

As illustrated in Table 3, the viscosity of 66# is significantly higher than that of Arista™.

Preferred Embodiment 3

A biocompatible modified starch material uses as hemostatic material. It includes pre-gelatinized hydroxypropyl distarch phosphate (51#). Its molecule weight is over 15,000 Dalton (15,000~2,000,000 Dalton). Diameter of its particles is 10~1000 μm. Particle diameter is between 50 and 500 μm in no less than 95% of the particles.

Preferred Embodiment 4

A biocompatible modified starch applied in hemostasis includes crosslinked carboxymethyl starch (66#+). Its molecule weight is over 15,000 Dalton (15,000~2,000,000 Dalton) and the diameter of particles is 10~1000 μm; among them, those with diameters between 50 and 500 μm take no less than 95% of total amount of starch particles.

Preferred Embodiment 5

A biocompatible modified starch uses as hemostatic material. It includes pre-gelatinized starch prepared using a spray drying process. Its molecule weight is over 15,000 Dalton (15,000~2,000,000 Dalton). Diameter of particles is 10~1000 μm, Particle diameter is between 50 and 500 μm in no less than 95% of the particles.

The water absorbency of various modified starch is determined by centrifugation and the results are illustrated in Table 4:

Water absorbency refers to the maximal water that 1 g sample can absorb.

Water absorbency (ml/g)=amount of absorbed water (ml)/amount of sample (g).

As illustrated in table 4, all prepared modified starches have better water absorbency.

Control Experiment 1

Hemostatic effects in a liver bleeding model in New Zealand rabbits.

Objective: To investigate the hemostatic effects of 66# products in a liver bleeding model in New Zealand rabbits.

Test Drugs:

Name: Product 66# (carboxymethyl starch hemostatic spheres)

Animals: New Zealand white rabbits, supplied by Laboratory Animal Center, the Second Military Medical University.

Certification Number: SCKK (SH) 2002-0006

A total of 15 animals were used (n=5 per group). Body weight: 2.0±0.3 kg.

Methods:

New Zealand white rabbits were randomly divided into 3 groups, a product 66# group, a positive control group (Arista™) and a negative control group (raw starch) (n=5, respectively). The rabbits were anaesthetized with sodium pentobarbital (40 mg/kg) via ear vein injection. Rabbits were fixed in a supine position. Hair was removed. After disinfection, the abdominal cavity was opened layer by layer to expose the liver sufficiently. A 1 cm diameter and 0.3 cm deep wound was produced using a puncher on the liver surface. Hemostatic material was applied immediately. The wound was pressed for 20 s. Hemostatic effects were observed in each animal group. The animals received Arista™ and raw starch in the positive control group and the negative control group, respectively. All the animals received un-restricted food and water after the surgery. At half an hour, one, two, three and seven days after surgery, one animal from each group was chosen and received anesthesia. The hepatic wound surface was stained with iodine to observe the degradation of the hemostatic materials. The wound tissue was taken out and fixed with 10% formaldehyde. Tissue sections were prepared and used to observe the degradation of the hemostatic materials.

Dosage: 50 mg/wound surface
Route: spray applying
Frequency: once/wound surface
Outcomes and observation time: hemostatic effect, absorption and degradation, healing of the wound surface. Observation times were: half an hour, one day, two days, three days and seven days after the surgery.

Figure 2:
FIG. 2 illustrates hemostatic effects of a modified starch carboxymethyl-starch 66# in a rabbit liver bleeding model.
Figure 3:
FIG. 3 illustrates hemostatic effects of raw starch in a rabbit liver bleeding model.

Results:
Effects on Hemostasis
In the positive control group (Arista™), the bleeding was stopped immediately after the hemostatic material was sprayed on. In the product 66# group, the bleeding was also stopped immediately. In the raw starch group, the bleeding could not be stopped after the hemostatic material was sprayed on even with wound pressing. (See FIGS. 1 to 3)

Degradation In Vivo
There was no iodine color reaction in the positive control group (Arista™) and product 66# group at half an hour. Color reaction was positive in the negative control group at half an hour later, but not 24 hours later.

Control Experiment 2

Degradation in Abdominal Cavity of Mice
Objective: To investigate the adhesion and degradation of product 66# in abdominal cavity of mice.
Test Drugs:
Name: Product 66# (carboxymethyl starch hemostatic spheres)
Animal: ICR mouse, supplied by Laboratory Animal Center, the Second Military Medical University.
Certification Number of Animals: SCXK (SH) 2002-0006
A total of 30 animals were used (n=10 per group). Body weight: 18-23 g. Half were females and half were males.
Methods: Product 66#, the positive control Arista™, and the negative control raw starch, were prepared into 0.1 g/ml solutions with normal saline. A total of 30 ICR mice were randomly divided into three groups, a product 66# group, a positive control group (Arista™) and a negative control group (raw starch). Animals received intraperitoneal injection of 1 ml of the above-mentioned solutions. Twenty-four hours later, abdominal cavity was opened. Iodine was applied in the abdominal cavity to observe color change and visceral adhesion. Animals in the positive control group and the negative control group received Arista™ and raw starch, respectively.

Dosage: 1 ml/per mouse
Route: intraperitoneal injection
Frequency: once/per mouse
Outcomes and observation time: The abdominal cavity was opened 24 hours after the administration to observe organ adhesion and material degradation.

Figure 4:
FIG. 4 illustrates adhesion in abdominal cavity in the experimental group (carboxymethyl starch 66#) 24 hours after the establishment of the mouse model.

Results:
Adhesion In Vivo
Twenty-four hours later, no organ adhesion was found in the abdominal cavity in 66# experimental group. (See FIG. 4)

Figure 5:
FIG. 5 illustrates degradation in abdominal cavity in the experimental group (carboxymethyl starch 66#) 24 hours after the establishment of the mouse model.

Degradation In Vivo
No iodine color reaction was found in 66# experimental group at twenty-four hours later, indicating that 66# had been degraded completely within the mice body. (See FIG. 5)

Control Experiment 3

An investigation of hemostastic effects of products 66# and 88# in a canine femoral artery bleeding model.
Objective: To observe the hemostatic effect of product 66# and 88# in serious trauma, and compare the hemostatic effect of product 66# and product 88# with Arista™.
Animals: experimental dogs.
A total of 20 male animals were used (n=5 per group). Body weight: 20-25 kg.
Methods: The animals were randomly divided into a control group (pressing with gauze), a product 66# group, a product 88# group, and an Arista™ group. The femoral artery was exposed and punctured with a No. 18 needle (diameter: 2F). Blood was allowed to flow freely for 2 second. After establishment of the canine femoral artery injury model, product 66#, 88#, or Arista™ (1 g, respectively) was applied on the bleeding sites and pressed manually. Animals in the control group received pressing with gauze. Then, after pressing for 60 s, 90 s, 120 s, and 180 s, hemostatic effects of the materials were observed. Successful cases were recorded. Stop of bleeding or blood oozing at the puncturing was used as a criterion for successful hemostasis. Hemostatic status of experimental animals under different hemostatic conditions is shown in Table 5.

Conclusion
Product 66#, 88# and Arista™ had significant hemostatic effects on canine femoral artery bleeding as compared with the control group. Product 66# and 88# had better sealing effects on the punctured site at femoral artery and significantly shorter hemostatic time than Arista™. Furthermore, the more adhesive product 88# had better sealing effects on the punctured site at femoral artery and shorter hemostatic time than product 66# and Arista™.

Control Experiment 4

An investigation on postoperative intestinal adhesion in rats.
A sample of product 66# in the experimental group was compared with a positive control of sodium hyaluronate on sale for medical use, and a blank control.
Experimental Animals and Grouping
Thirty-four male SD rats weighing 200~250 g were supplied by Laboratory Animal Center, the Fourth Military Medical University. They were divided into three groups: a blank control group, a 66# group, and a positive control group of medical sodium hyaluronate (SH). Each group consists of 11 or 12 rats.
Preparation of the Rat Intestinal Adhesion Model
Animals in all groups were fasted but received unrestricted supply of water 12 hours before the operation. Rats were anaesthetized with 3% sodium pentobarbital (30 mg/kg; intramuscular). The cecum was exposed through a 2 cm midline incision in the lower abdomen. The serosa of the cecum was scraped until blood oozed. Anhydrous ethanol was applied on the wound surface. The mesenteric artery of cecum was clamped with a 5-finger clamp for 2 min to induce temporary ischemia. After these treatments, the wound surface in the 66# group and SH group were covered with the corresponding drugs. The blank controls did not receive any drug. The cecum was placed back into the original position in the abdominal cavity. The opposing abdominal wall was damaged with a hemostatic forcep and the abdominal cavity was closed with No. 1-0 thread layer by layer. Rats received intramuscular gentamicin injection (4U) for 3 consecutive days after the surgery to prevent infection. Fourteen days later, the same method of anesthesia was used to open the abdominal cavity for examination and sampling.

Relevant Measurements

1) General Condition: Survival of the rats was recorded after the operation.

2) Intestinal Adhesion: The abdominal cavity was opened using a U-shaped incision (bottoms down) that included the original midline incision. The tissue flap was lifted up to expose the abdominal cavity. Adhesion between the cecum and the abdominal wall was observed and graded using the Nair 5 Grading System: Grade 0: no adhesion; Grade 1: one adhesion belt between the viscera or between different points of the abdominal wall; Grade 2: two adhesion belts between the viscera or between the viscera and abdominal wall; Grade 3: two adhesion belts; no direct adhesion of the viscera to the abdominal wall; Grade 4: the viscera adhere to the abdominal wall directly, regardless of the number of adhesion belt.

Figure 6:
FIG. 6 illustrates intestinal adhesion in the control rat group (blank).
Figure 7:
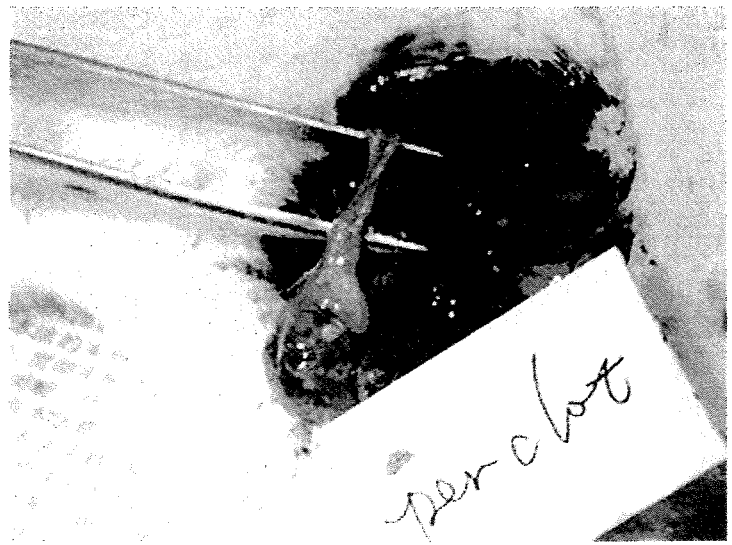
FIG. 7 illustrates preventive effects of modified starch-carboxymethyl starch 66# on intestinal adhesion in rats.
Figure 8:
FIG. 8 illustrates preventive effects of sodium hyaluronate (positive control) on intestinal adhesion in rats.

Please refer to FIG. 6 for the intestinal adhesion in the blank control group. FIG. 7 illustrates the effects of 66# in preventing intestinal adhesion. FIG. 8 illustrates the effects of sodium hyaluronate in preventing intestinal adhesion. These results indicated that the sodium hyaluronate and carboxymethyl starch 66# could significantly reduce postoperative intestinal adhesion in rats.

Control Experiment 5

An investigation on the postoperative bone healing condition in rabbits

Experimental Method

Major Materials

Carboxymethyl starch 66#, pre-gelatinized hydroxypropyl distarch phosphate 51#, bone wax, and blank control group.

Experimental Animals and Grouping

32 New Zealand adult female rabbits, 2.0~2.5 kg, were supplied by Laboratory Animal Center of the Fourth Military Medical University. Two defect pores could be drilled on each animal. The rabbits were randomly divided into a blank control group, a 66# group, a 51# group, and a bone wax group (n=8, respectively).

Operative Method

Animals were anaesthetized with 3% sodium pentobarbital via the ear vein injection (30 mg/kg) and fixed on a prone position on an operative table. A 4 cm sagital incision was made along the midline to expose the skull. The periosteum was removed completely. A round defect pores was made on each side of cranial midline with a 6 mm diameter drill bit (diameter: 6 mm) The defects spanned the layer of the skull (The thickness of the skull is essentially uniform in parietal bone). The midline was not crossed. The defects were covered randomly with one of the aforementioned materials. No material was applied in the control group. The periosteum and scalp were sutured with absorbable 4-0 thread. The wound was aseptically dressed. Animals were placed back to the home cage and raised for 6 weeks. Animals received intramuscular gentamicin injection (4U) 3 consecutive days after the surgery to prevent infection. The general situation of the animals was monitored everyday.

Seven days prior to the sacrifice, animals received calcein (Sigma, dissolved in 2% sodium bicarbonate) via the ear veins (20 mg/kg). At 1 day to the sacrifice, animals received tetracycline (30 mg/kg; Sigma, dissolved in double distilled water) via the ear vein on the other side. Calcein and tetracycline were deposited on the mineralizing front of newly formed bone matrix, thus could be used as markers to measure the growth range of the bone during the six days.

Sampling and the Assessment for Bone Healing

1. Sampling: Six weeks after the operation, the animals were sacrificed with excessive intravenous pentobarbital injection. The skull covering at least 1.5 cm from the defect edge was included. The samples included periosteum and cerebral dura mater. The samples were fixed with 70% alcohol.

2. Bone Healing Score: Bone healing of all defects was assessed with healing score. The standards were: 0=no visible defect; 1=a few visible defects; 2=moderate visible defects; 3=extensive visible defects.

3. Pathology and Immunohistochemistry: Fixed skull sample was embedded with paraffin. Sections were prepared using routine methods, observed and photographed using an ultraviolet fluorescent microscope. The fluorescent markers, calcein and tetracycline, bind to the newly formed bone matrix and that not calcified yet, respectively, thus showing linear fluorescence. The distance between the two fluorescent labeling lines indicates mineral apposition rate (MAR) during the 6 days and activity of osteoblasts, (osteogenetic speed).

$$MAR = \frac{\text{Distance between two fluorescent labeling lines } (\mu m)}{\text{Days between two administrations}}$$

Sections were deparaffinated, dehydrated, transparentized and stained with Goldner-Mason-Trichrome and ponceau. The osteoid area and mineralization bone area were labeled in different colors, and were observed under a light microscope, photographed. Areas stained with different materials were analyzed with image analysis software.

$$\text{Osteoid Rate} = \frac{\text{Osteoid area of defect pore}}{\text{Area of defect pore}}$$

$$\text{Mineralization Bone Rate} = \frac{\text{Mineralization bone area of defect pore}}{\text{Area of defect pore}}$$

$$\text{Defect Area Rate} = \frac{\text{congenital absence area of defect pore}}{\text{Area of defect pore}}$$

4. Evaluation Criteria: Bone healing score, mineral deposition rate, the osteoid area, mineralization bone area, and congenital absence area.

5. Statistical Analysis

Data were treated with SPSS 11.0 statistical software. Analysis of variance was employed in the comparison of data among the groups.

Experimental Results

Result

The healing score of defects in 51# group and 66# group was significantly lower than that in the blank control group and the bonewax group at the sixth week after the operation. The mineral deposition rate, osteoid area, mineralization bone area and other indexes in 51# group and 66# group were significantly higher than those in the blank control group, whereas the congenital absence area in 51# group and 66# group was significantly lower than that in the blank control group.

Figure 9:
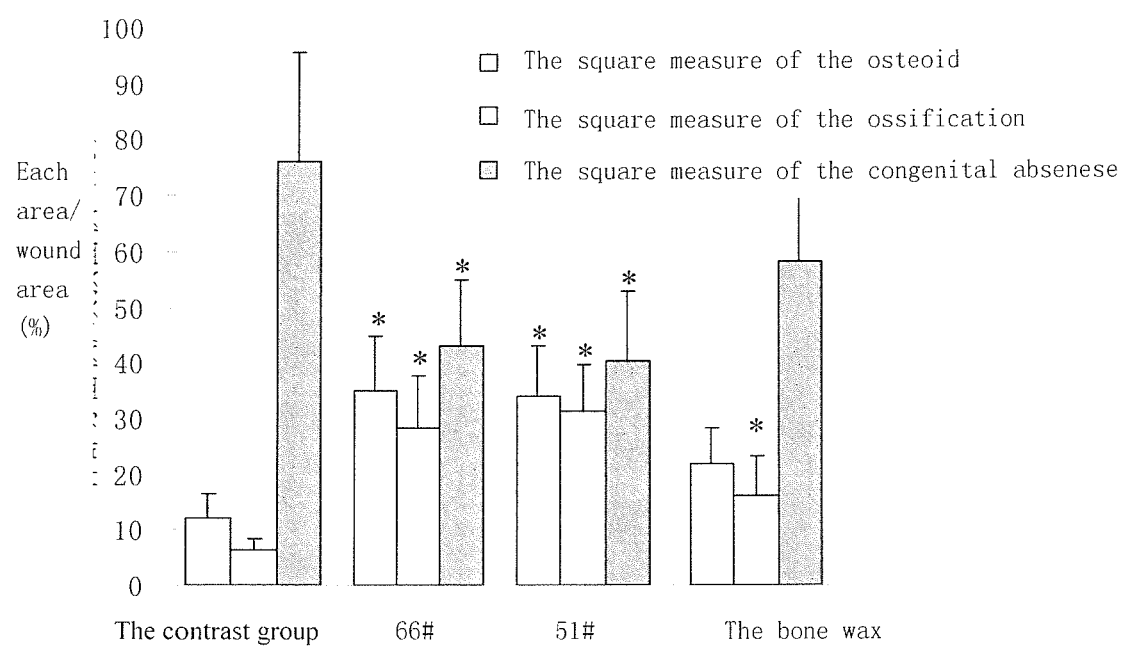
FIG. 9 illustrates a comparison of bone healing indexes in rabbits.

As shown in FIG. 9, a representative photograph for bone healing indexes in rabbits, 66# and 51# had remarkable effects in improving the skull healing in rabbits.

B. Modified Starch Sponge

Preferred Embodiment 6

Two gram pre-gelatinized hydroxypropyl distarch phosphate 51# is added into 30 ml water and stirred continuously to make starch particles swell sufficiently and disperse into a uniform suspension. Several drops of glycerol are added as a plasticizing agent (forming agent). The liquid is then put in a container and pre-cooled at −40° C. for 22 hours. It is then frozen and dried for 20 hours at −40° C. in a vacuum <20 Pa in a freezing drier. The final product is modified starch composite hemostatic sponge A.

Preferred Embodiment 7

One gram pre-gelatinized hydroxypropyl distarch phosphate 51# is added into 30 ml water and stirred continuously to make starch particles swell sufficiently and disperse into a uniform suspension. The liquid is then put in a container and precooled at −40° C. for 22 hours. It is then frozen and dried for 20 hours at −50° C. in a vacuum <20 Pa in a freezing drier. The final product is modified starch composite hemostatic sponge B.

Figure 10:
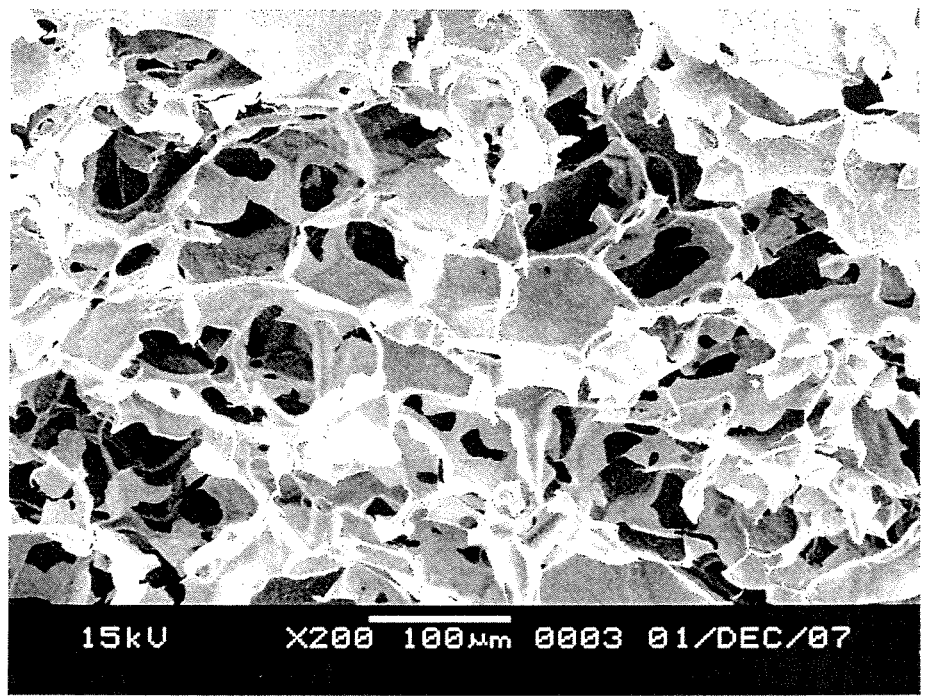
FIG. 10 illustrates a representative scanning electron microscope photo of section of pre-gelatinized hydroxypropyl distarch phosphate (51#) hemostatic sponge A.
Figure 11:
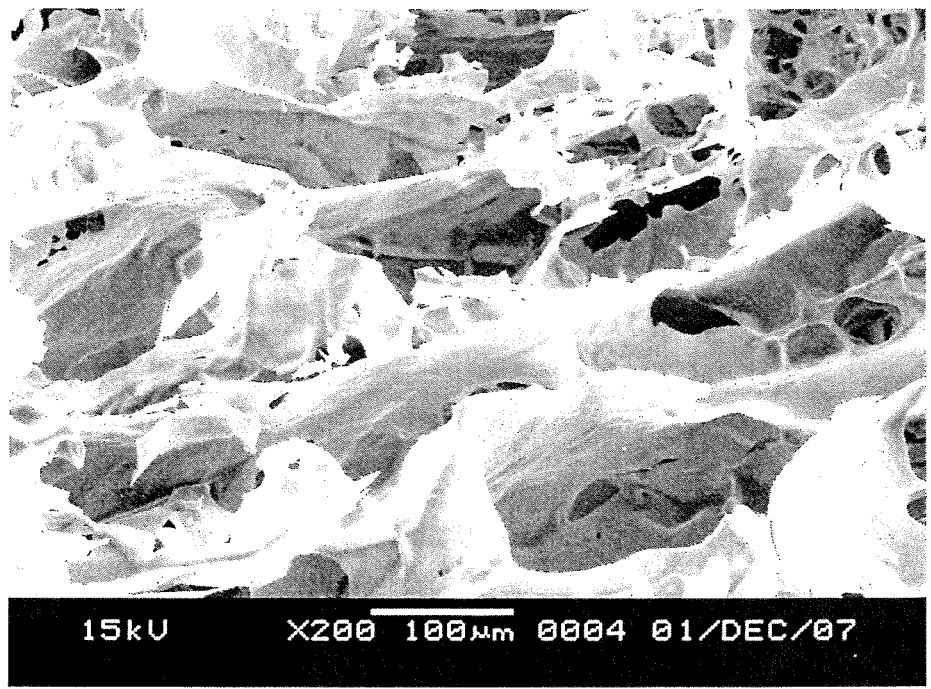
FIG. 11 illustrates a representative scanning electron microscope photo of section of pre-gelatinized hydroxypropyl distarch phosphate (51#) hemostatic sponge B.

Referring to FIG. 10, a scanning electron microscope photo for the section of hemostatic sponge A is illustrated, and referring to FIG. 11, a scanning electron microscope a photo for the section of hemostatic sponge B is illustrated. Adding plasticizing agent during production can reduce sponge pore's diameters and enhance its density and specific surface area.

Preferred Embodiment 8

Two gram carboxymethyl starch 66# is added into 30 ml water and stirred continuously to make starch particles swell sufficiently and disperse into a uniform suspension. The liquid is then put in a container and precooled at −40° C. for 22 hours. It is then frozen and dried for 20 hours at −50° C. in a vacuum <20 Pa in a freezing drier. The final product is modified starch composite hemostatic sponge C.

Preferred Embodiment 9

Three gram crosslinked carboxymethyl starch 66#+ is added into 30 ml water and stirred continuously to make starch particles swell sufficiently and disperse into a uniform suspension. The liquid is then put in a container and pre-cooled at −40° C. for 22 hours. It is then frozen and dried for 20 hours at −45° C. in a vacuum <20 Pa in a freezing drier. The final product is modified starch composite hemostatic sponge D.

Preferred Embodiment 10

Three gram hydroxyethyl starch 88# is added into 30 ml water and stirred continuously to make starch particles swell sufficiently and disperse into a uniform suspension. The liquid is then put in a container and precooled at −40° C. for 22 hours. It is then frozen and dried for 20 hours at −50° C. in a vacuum <20 Pa in a freezing drier. The final product is modified starch composite hemostatic sponge E.

Preferred Embodiment 11

A certain amount of medical gelatin (10 g) is added into 100 ml water and heated in a beaker to 60° C. to form a colloidal solution. Two gram carboxymethyl starch 66# is added into 30 ml water and stirred continuously to make starch particles swell sufficiently and disperse into a uniform suspension. The two solutions are mixed together in a container with the mass ratio of medical gelatin to 66# at 1:1. After precooling at −40° C. for 22 hours, it is frozen and dried for 20 hours under −45° C. in a vacuum <20 Pa in a freezing drier. The final product is modified starch composite hemostatic sponge F.

Preferred Embodiment 12

A certain amount of medical gelatin (10 g) is added into 100 ml water and heated in a beaker to 60° C. to form a colloidal solution. Two gram carboxymethyl starch 66# is added into 30 ml water and stirred continuously to make starch particles swell sufficiently and disperse into a uniform suspension. The two solutions are mixed together in a container with the mass ratio of medical gelatin to 66# at 2:1. After precooling at −40° C. for 22 hours, it is frozen and dried for 20 hours under −45° C. in a vacuum <20 Pa in a freezing drier. The final product is modified starch composite hemostatic sponge G.

Preferred Embodiment 13

A certain amount of medical gelatin (10 g) is added into 100 ml water and heated in a beaker to 60° C. to form a colloidal solution. One gram hydroxypropyl distarch phosphate 51# is added into 30 ml water, and stirred continuously to make starch particles swell sufficiently and disperse into a uniform suspension. The two solutions are mixed together in a container with the mass ratio of medical gelatin to hydroxypropyl distarch phosphate 51# at 2:1. After precooling at −40° C. for 22 hours, it is frozen and dried for 20 hours under −45° C. in a vacuum <20 Pa in a freezing drier. The final product is modified starch composite hemostatic sponge H.

Preferred Embodiment 14

A certain amount of medical gelatin (10 g) is added into 100 ml water and heated in a beaker to 60° C. to form a colloidal solution. One gram hydroxypropyl distarch phosphate 51# is added into 30 ml water and stirred continuously to make starch particles swell sufficiently and disperse into a uniform suspension. The two solutions are mixed together in a container with the mass ratio of medical gelatin to hydroxypropyl distarch phosphate 51# at 1:1. After precooling at −40° C. for 22 hours, it is frozen and dried for 20 hours under −45° C. in a vacuum <20 Pa in a freezing drier. The final product is modified starch composite hemostatic sponge I.

0.1 g of the above-mentioned sponges is used to compare the chemical and physical property. Results are shown in Table 8.

An introduction to the measurement of contact angle

Apparatus: OCA40 Micro video contact angle measuring system (Dataphysics, Germany)

Methods: A sessile drop method was used to track and record water absorbing status of sponges using dynamic recording function and camera function. Details of the procedure were: a sponge sample was placed on an object table, and adjusted slowly to make the object stage appear at the inferior ⅓ portion of the visual field. A needle filled with deionized water connected an injection unit was used. A drop of water with a certain volume was suspended at the tip of the needle using an automatic injection system. The system was focused so that the image of the sponge sample and water drop appeared clearly in the visual field. The object table was raised slowly so that the sponge sample touched the water drop. The camera function and dynamic recording function were turned on simultaneously to observe the process of water drop being absorbed and obtain the dynamic contact angle values.

The water absorption ability of composite hemostatic sponges is shown in Table 9.

Water absorbency of the sponges is determined by centrifugation. 0.025 g sponge was placed in 2 ml water, equilibrated for 10 minutes, and centrifuged for 10 minutes at 500 rpm. Sample was taken out, and weighed. The amount of remaining residual liquid was calculated. Each sample was measured 6 times. Average values were used.

Volume density of sponges was measured. A sponge sample was cut into certain length and width and height, and weighed to calculate the density.

Hygroscopicity and water absorbency of the sponges were observed through the OCA40 Micro video contact angle measuring system of Dataphysics, Germany.

A comparison of water absorbency between composite hemostatic sponges and other hemostatic sponges is shown in Table 10.

As shown in Table 10, composite hemostatic sponge containing modified starch had significantly higher water absorbency than gelatin sponge and collagen hemostatic sponge. Composite hemostatic sponge's maximal water absorbency could reach 2~5 times higher than normal gelatin sponge and collagen hemostatic sponge could. They absorbed water faster and more efficiently and retained high water absorbency in the fifth and sixth 20 s.

Control Experiment 6

Animal Experiment

Objective: To observe the hemostatic effect of modified starch hemostatic sponge in a liver bleeding models.

Experimental Method

An area of 2 cm×1 cm was cut off with a scalpel on the liver surface. Wound depth was 0.3 cm. Hemostatic sponges employed in the experiment to stop bleeding of the wound were: 51# hemostatic sponge B, 66# hemostatic sponge C, composite hemostatic sponge I [51#: medical gelatin (mass ratio): 1:1], composite hemostatic sponge F [66#: gelatin (mass ratio) 1:1], composite hemostatic sponge [66#: carboxymethyl cellulose (mass ratio): 1:1], and composite hemostatic sponge [66#: collagen (mass ratio) 10:1]. Simple gelatin sponge and collagen sponge were used as controls. When the wound started to bleed, the hemostatic sponges were immediately placed on the wound. A medical surgical glove or hemostatic gauze was used to press the wound and to stop the blood stream. 1~2 min later, the glove or gauze was released gently to observe the hemostatic effect and whether the glove or the gauze had adhered to the sponge or the blot clot and whether re-bleeding occurred as the glove or gauze was removed. It was unnecessary to remove modified starch sponge after the bleeding was stopped. The wound was gently irrigated with normal saline.

Results:

All hemostatic sponges containing modified starch in the experimental groups had satisfactory hemostatic effect and were convenient to use. Sponges in the experimental groups can absorb moisture/blood immediately and form an adhesive sponge-blood coagulation colloid with the blood. Effective control of the bleeding from the liver wound was achieved in 1-2 minutes, in comparison to 3-5 min or more with the gelatin sponge and collagen sponge. Upon contact with the blood, hemostatic sponges in the experimental groups can adhere to the liver wound tissue tightly to promote blood coagulation and seal the bleeding vessels on the wound surface. The sponges in the experimental groups are elastic and easy to use. They do not adhere to the glove or gauze that are used to press the wound, and do not destroy the blood clot when the glove or gauze is removed, and therefore do not cause re-bleeding. The gelatin sponge and collagen hemostatic sponge in the control groups absorbed moisture/blood slowly, and needed to be pressed for multiple times. They adhered poorly to the tissue of wound surface, and had poor hemostatic effects.

One skilled in the art will understand that the embodiments of present invention, as shown in the drawings and described above are exemplary only and not intended to be limited.

It will thus be seen that the objectives of the present invention have been fully and effectively achieved. The embodiments have been shown and described for the purposes of illustrating the functional and structural principles of the present invention and are subject to change without departure from such principles. Therefore, this invention includes all modifications encompassed within the spirit and scope of the following claim.

What is claimed is:

1. A biocompatible modified starch for effecting hemostasis, anti-adhesion therapy, tissue healing promotion, wound sealing, and wounded tissue bonding by applying directly onto the wounded tissue of the animal, wherein the biocompatible modified starch is a hemostatic powder consisting essentially of biocompatible modified starch particles having water absorbency capacity not lower than 1 times its own particle weight and a molecular weight 10,000 Daltons or more and a grain diameter of 10 to 1000 μm, wherein the hemostatic powder has an adhesiveness sufficient that the hemostatic powder forms a starch-blood coagulation upon contacting the wounded tissue when being applied directly onto the wounded tissue of the animal, wherein the biocompatible modified starch contains one or more groups of pre-gelatinized starch, acid modified starch, oxidized starch, esterified starch, and cross-linked starch, wherein the biocompatible modified starch contains at least pre-gelatinized hydroxypropyl distarch phosphate in pre-gelatinization modification.

2. A biocompatible modified starch for effecting hemostasis, anti-adhesion therapy, tissue healing promotion, wound sealing, and wounded tissue bonding by applying directly onto the wounded tissue of the animal, wherein the biocompatible modified starch is a hemostatic powder consisting essentially of biocompatible modified starch particles having water absorbency capacity not lower than 1 times its own particle weight and a molecular weight 10,000 Daltons or more and a grain diameter of 10 to 1000 μm, wherein the hemostatic powder has an adhesiveness sufficient that the hemostatic powder forms a starch-blood coagulation upon contacting the wounded tissue when being applied directly onto the wounded tissue of the animal, wherein the biocompatible modified starch particles have starch grains with grain diameter 30 to 500 μm, at least 95% starch grains in said hemostatic powder with a diameter 30 to 500 μm of in total, wherein the biocompatible modified starch contains one or more groups of pre-gelatinized starch, acid modified starch, oxidized starch, esterified starch, and cross-linked starch, wherein the biocompatible modified starch contains at least pre-gelatinized hydroxypropyl distarch phosphate in pre-gelatinization modification.

3. A biocompatible modified starch for effecting hemostasis, anti-adhesion therapy, tissue healing promotion, wound sealing, and wounded tissue bonding by applying directly onto the wounded tissue of the animal, wherein the biocompatible modified starch is a hemostatic powder consisting essentially of biocompatible modified starch particles having water absorbency capacity not lower than 1 times its own particle weight and a molecular weight 10,000 Daltons or more and a grain diameter of 10 to 1000 μm, wherein the hemostatic powder has an adhesiveness sufficient that the hemostatic powder forms a starch-blood coagulation upon contacting the wounded tissue when being applied directly onto the wounded tissue of the animal, wherein said biocompatible modified starch contains one or more groups of pre-gelatinized starch, acid modified starch, oxidized starch, esterified starch, and cross-linked starch, wherein the biocompatible modified starch contains at least one carboxymethyl starch, hydroxyethyl starch, and cationic starch in pre-gelatinization modification.

4. A biocompatible modified starch for effecting hemostasis, anti-adhesion therapy, tissue healing promotion, wound sealing, and wounded tissue bonding by applying directly onto the wounded tissue of the animal, wherein the biocompatible modified starch is a hemostatic powder consisting essentially of biocompatible modified starch particles having water absorbency capacity not lower than 1 times its own particle weight and a molecular weight 10,000 Daltons or more and a grain diameter of 10 to 1000 μm, wherein the hemostatic powder has an adhesiveness sufficient that the hemostatic powder forms a starch-blood coagulation upon contacting the wounded tissue when being applied directly onto the wounded tissue of the animal, wherein the biocompatible modified starch particles have starch grains with grain diameter 30 to 500 μm, at least 95% starch grains in said hemostatic powder with a diameter 30 to 500 μm of in total, wherein the biocompatible modified starch contains one or more groups of pre-gelatinized starch, acid modified starch, oxidized starch, esterified starch, and cross-linked starch, wherein the biocompatible modified starch contains at least one carboxymethyl starch, hydroxyethyl starch, and cationic starch in pre-gelatinization modification.

* * * * *